(12) United States Patent
Yao et al.

(10) Patent No.: US 12,364,440 B2
(45) Date of Patent: Jul. 22, 2025

(54) SUPERVISED MACHINE LEARNING BASED MULTI-TASK ARTIFICIAL INTELLIGENCE CLASSIFICATION OF RETINOPATHIES

(71) Applicant: The Board of Trustees of the University of Illinois, Urbana, IL (US)

(72) Inventors: Xincheng Yao, Chicago, IL (US); Minhaj Alam, Chicago, IL (US); Tae Yun Son, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 774 days.

(21) Appl. No.: 17/438,700

(22) PCT Filed: Mar. 13, 2020

(86) PCT No.: PCT/US2020/022774
§ 371 (c)(1),
(2) Date: Sep. 13, 2021

(87) PCT Pub. No.: WO2020/186222
PCT Pub. Date: Sep. 17, 2020

(65) Prior Publication Data
US 2022/0151568 A1 May 19, 2022

Related U.S. Application Data

(60) Provisional application No. 62/840,061, filed on Apr. 29, 2019, provisional application No. 62/818,065, filed on Mar. 13, 2019.

(51) Int. Cl.
*A61B 3/02* (2006.01)
*A61B 3/10* (2006.01)
(Continued)

(52) U.S. Cl.
CPC ............ *A61B 5/7275* (2013.01); *A61B 3/102* (2013.01); *A61B 3/1241* (2013.01);
(Continued)

(58) Field of Classification Search
CPC ......... A61B 3/02; A61B 3/1025; A61B 3/102; A61B 3/113; A61B 3/0075; A61B 3/1225; A61B 3/1015; A61B 3/005; A61B 3/0243
(Continued)

(56) References Cited

U.S. PATENT DOCUMENTS 9,984,459 B2 5/2018 Reisman
10,194,866 B2 2/2019 Hsiao
(Continued)

FOREIGN PATENT DOCUMENTS

WO 2010131944 A2 11/2010
WO 2017031099 A1 3/2017
(Continued)

OTHER PUBLICATIONS

European Search Report, EP Patent Application No. 20771123.5, mailed Nov. 28, 2022.
(Continued)

*Primary Examiner* — Dawayne Pinkney
(74) *Attorney, Agent, or Firm* — Thomas | Horstemeyer, LLP

(57) ABSTRACT

An artificial intelligence (AI) system is disclosed that uses machine learning to classify retinal features contained in OCTA data acquired by a data acquisition system and to predict one or more retinopathies based on the classification of retinal features. The AI system comprise a processor configured to run a classifier model comprising a machine learning algorithm and a memory device that stores the classifier model, OCTA training data and acquired OCT A
(Continued)

data. The machine learning algorithm performs a process that trains the classifier model to classify retinal features contained in OCT A training data. The trained machine learning algorithm uses the classifier model to process acquired OCT A data to classify retinal features contained in the acquired OCTA data and to predict, based on the classified retinal features, whether the acquired OCTA data is indicative of at least one of a plurality of retinopathies.

13 Claims, 30 Drawing Sheets

(51) Int. Cl.
  A61B 3/12     (2006.01)
  A61B 5/00     (2006.01)
  A61B 5/02     (2006.01)
  G16H 30/20    (2018.01)
  G16H 30/40    (2018.01)
  G16H 50/20    (2018.01)
  G16H 50/70    (2018.01)

(52) U.S. Cl.
  CPC ........ *A61B 5/02007* (2013.01); *A61B 5/7267* (2013.01); *G16H 30/20* (2018.01); *G16H 30/40* (2018.01); *G16H 50/20* (2018.01); *G16H 50/70* (2018.01)

(58) Field of Classification Search
  USPC ............... 351/246, 200, 205, 206, 208–210, 351/221–223
  See application file for complete search history.

(56) References Cited

U.S. PATENT DOCUMENTS

| | | | |
|---|---|---|---|
| 10,603,040 B1* | 3/2020 | Berman | A61B 18/1492 |
| 2006/0077348 A1 | 4/2006 | Gorin | |
| 2015/0110348 A1 | 4/2015 | Solanki et al. | |
| 2016/0183786 A1 | 6/2016 | Wei et al. | |
| 2017/0294015 A1* | 10/2017 | Wang | G06T 7/0012 |
| 2018/0140180 A1* | 5/2018 | Coleman | G06T 7/0012 |
| 2018/0315193 A1 | 11/2018 | Pachalakis et al. | |
| 2019/0151337 A1* | 5/2019 | Tsuruda | A61P 27/02 |
| 2019/0272631 A1* | 9/2019 | Shemonski | A61B 3/102 |
| 2020/0069175 A1* | 3/2020 | Kumagai | A61B 3/0025 |
| 2020/0273218 A1* | 8/2020 | Camino | G16H 50/20 |
| 2021/0369195 A1* | 12/2021 | Russakoff | G16H 30/40 |

FOREIGN PATENT DOCUMENTS

| | | |
|---|---|---|
| WO | 2018069768 A2 | 4/2018 |
| WO | 2018237011 A1 | 12/2018 |

OTHER PUBLICATIONS

Phan, Thanh Van, et al., "Towards an Automatic Clinical Classification of Age-Related Macular Degeneration," SAT 2015 18th International Conference, Sep. 24-27, 2015, Lecture Notes in Computer Science, pp. 352-359.

Welikala, R. A., et al., "Genetic algorithm based feature selection combined with dual classification for the automated detection of proliferative diabetic retinopathy," Computerized Medical Imaging and Graphics, vol. 43, No. 20 (2015), pp. 64-77.

Abbas, Qaisar, et al., "Automatic recognition of severity level for diagnosis of diabetic retinopathy using deep visual features," Medical and Biological Engineering and Computing, vol. 55, No. 11 (2017), pp. 1959-1974.

International Search Report for PCT/US20/022774 mailed Jul. 30, 2020.

Kozak, et al., "Machine Learning Classifiers Detect Subtle Field Defects in Eyes of HIV Individuals", Trans Am Ophthalmol Soc. Dec. 2007.

Daniel Shu Wei Ting et al., "Artificial intelligence and deep learning in ophthalmology", (Br J Ophthalmol, Feb. 2019;103(2):167-175. Epub Oct. 25, 2018).

Jeffrey De Fauw et al., "Clinically applicable deep learning for diagnosis and referral in retinal disease" (Nat Med, Sep. 2018;24(9):1342-1350. Epub Aug. 13, 2018).

Minhaj Alam et al., "Color Fundus Image Guided Artery-Vein Differentiation in Optical Coherence Tomography Angiography"(Invest Ophthalmol Vis Sci, Oct. 1, 2018;59(12):4953-4962).

S. Maheswari et al., "Classification of Retinal Vessels into Arteries and Veins—a survey" (International Journal on Computational Sciences & Applications (IJCSA) vol. 4, No. 6, Dec. 2014).

Minhaj Alam et al., "OCT feature analysis guided artery-vein differentiation in OCTA" (Biomed Opt Express, Mar. 26, 2019;10(4):2055-2066.).

* cited by examiner

TABLE 1

| | Control | DR | | | SCR | |
|---|---|---|---|---|---|---|
| | | Mild NPDR | Moderate NPDR | Severe NPDR | Mild SCR | Severe SCR |
| Number of subjects | 20 | 20 | 20 | 20 | 30 | 18 |
| Sex (male) | 12 | 11 | 12 | 11 | 17 | 11 |
| Age (mean ± SD) | 42 ± 9.8 | 50.1 ± 12.61 | 50.8 ± 8.39 | 57.84 ± 10.37 | 51 ± 11.52 | 59.73 ± 8.26 |
| Age range | 25-71 | 24-74 | 32-68 | 41-73 | 28-71 | 46-75 |
| Duration of disease | - | 19.64 ± 13.27 | 16.13 ± 10.58 | 23.40 ± 11.95 | 13.25 ± 8.78 | 18.43 ± 10.7 |
| Diabetes type | - | Type II | Type II | Type II | - | - |
| Insulin dependent (Y/N) | - | 7/13 | 12/8 | 15/5 | - | - |
| HbA1C, % | - | 6.5 ± 0.6 | 7.3 ± 0.9 | 7.8 ± 1.3 | - | - |
| HTN prevalence, % | 10 | 45 | 80 | 80 | - | - |

[a] DR, diabetic retinopathy; SD, standard deviation; HbA1C, Glycated hemoglobin; HTN, hypertension

FIG. 2

TABLE 2

Univariate analysis

Univariate analysis of individual OCTA features for control, DR and SCR cohorts.

| | Control | DR | SCR | P values | | |
|---|---|---|---|---|---|---|
| | | | | Control vs. DR | Control vs. SCR | DR vs. SCR |
| BVT (SCP) | 1.11 ± 0.07 | 1.18 ± 0.04 | 1.25 ± 0.08 | 0.016 | <0.001 | 0.022 |
| BVC (μm)(SCP) | 17.47 ± 1.9 | 20.32 ± 3.8 | 21.43 ± 2.4 | 0.024 | 0.019 | 0.836 |
| VPI (SCP) | 10.26 ± 1.32 | 8.76 ± 2.60 | 8.43 ± 0.79 | 0.012 | 0.036 | 0.325 |
| BVD (%) | | | | | | |
| C1 (SCP), 2mm | 40.16 ± 10.32 | 35.61 ± 8.11 | 36.08 ± 7.02 | 0.019 | 0.051 | 0.154 |
| C2 (SCP), 4mm | 47.53 ± 6.32 | 40.72 ± 4.17 | 44.24 ± 5.52 | <0.001 | 0.019 | 0.017 |
| C3 (SCP), 6mm | 47.96 ± 2.36 | 38.89 ± 3.31 | 42.84 ± 3.24 | <0.001 | <0.001 | 0.014 |
| C1 (DCP), 2mm | 42.72 ± 13.19 | 38.98 ± 6.09 | 40.28 ± 10.17 | 0.024 | 0.058 | 0.208 |
| C2 (DCP), 4mm | 49.16 ± 5.78 | 43.32 ± 7.09 | 43.20 ± 4.17 | <0.001 | 0.011 | 0.095 |
| C3 (DCP), 6mm | 48.97 ± 3.18 | 41.75 ± 6.53 | 43.29 ± 4.30 | <0.001 | <0.001 | 0.005 |
| FAZ-A (SCP), mm² | 0.30 ± 0.06 | 0.39 ± 0.04 | 0.43 ± 0.05 | 0.006 | <0.001 | 0.008 |
| FAZ-A (DCP), mm² | 0.39 ± 0.08 | 0.52 ± 0.06 | 0.54 ± 0.06 | 0.006 | 0.005 | 0.059 |
| FAZ-CI (SCP) | 1.14 ± 0.11 | 1.38 ± 0.13 | 1.47 ± 0.14 | <0.001 | <0.001 | 0.004 |
| FAZ-CI (DCP) | 1.18 ± 0.12 | 1.41 ± 0.10 | 1.53 ± 0.13 | <0.001 | <0.001 | 0.002 |

*All values are presented as mean ± SD

FIG. 3

TABLE 3

|  | Mild NPDR | Moderate NPDR | Severe NPDR | P values Mild vs. Moderate | P values Moderate vs. Severe | P values Severe vs. Mild |
|---|---|---|---|---|---|---|
| BVT (SCP) | 1.14 ± 0.05 | 1.17 ± 0.06 | 1.23 ± 0.04 | 0.260 | 0.546 | 0.017 |
| BVC (μm)(SCP) | 18.06 ± 1.9 | 21.04 ± 2.2 | 21.86 ± 1.7 | 0.036 | 0.213 | 0.011 |
| VPI (SCP) | 9.94 ± 0.38 | 8.56 ± 0.15 | 7.79 ± 0.21 | 0.025 | 0.044 | <0.001 |
| BVD (%) |  |  |  |  |  |  |
| C1 (SCP), 2mm | 36.62 ± 9.03 | 36.01 ± 5.81 | 34.20 ± 9.38 | 0.019 | 0.154 | 0.041 |
| C2 (SCP), 4mm | 44.36 ± 6.72 | 40.81 ± 5.22 | 36.98 ± 6.50 | <0.001 | <0.001 | 0.005 |
| C3 (SCP), 6mm | 43.85 ± 3.38 | 38.95 ± 4.65 | 33.87 ± 4.24 | <0.001 | <0.001 | 0.014 |
| C1 (DCP), 2mm | 40.88 ± 10.37 | 38.78 ± 7.01 | 37.29 ± 8.16 | 0.042 | 0.658 | 0.018 |
| C2 (DCP), 4mm | 47.42 ± 4.83 | 43.39 ± 6.39 | 39.16 ± 7.25 | <0.001 | 0.026 | <0.001 |
| C3 (DCP), 6mm | 41.75 ± 11.08 | 42.32 ± 7.45 | 37.73 ± 5.29 | <0.001 | 0.006 | <0.001 |
| FAZ-A (SCP), mm² | 0.33 ± 0.05 | 0.38 ± 0.07 | 0.46 ± 0.06 | 0.018 | <0.001 | <0.001 |
| FAZ-A (DCP), mm² | 0.46 ± 0.07 | 0.53 ± 0.12 | 0.58 ± 0.09 | <0.001 | 0.003 | <0.001 |
| FAZ-CI (SCP) |  |  |  | <0.001 | 0.002 | <0.001 |
| FAZ-CI (DCP) |  |  |  | <0.001 | 0.009 | 0.002 |

FIG. 4

TABLE 4

| | Mild SCR | Severe SCR | P values (Mild vs. severe) |
|---|---|---|---|
| BVT (SCP) | 1.22 ± 0.07 | 1.28 ± 0.05 | <0.001 |
| BVC (μm) (SCP) | 18.82 ± 3.1 | 24.05 ± 2.6 | 0.385 |
| VPI (SCP) | 9.21 ± 0.26 | 9.64 ± 0.29 | 0.521 |
| BVD (%) | | | |
| C1 (SCP), 2mm | 36.99 ± 6.13 | 35.16 ± 8.08 | 0.163 |
| C2 (SCP), 4mm | 46.35 ± 4.53 | 42.13 ± 8.29 | 0.097 |
| C3 (SCP), 6mm | 46.85 ± 6.29 | 38.83 ± 3.23 | 0.018 |
| C1 (DCP), 2mm | 41.88 ± 10.85 | 38.68 ± 11.26 | 0.364 |
| C2 (DCP), 4mm | 47.06 ± 7.89 | 37.4 ± 8.36 | 0.073 |
| C3 (DCP), 6mm | 46.05 ± 6.25 | 40.5 ± 6.23 | 0.004 |
| FAZ-A (SCP), mm² | 0.41 ± 0.19 | 0.45 ± 0.12 | <0.001 |
| FAZ-A (DCP), mm² | 0.52 ± 0.19 | 0.56 ± 0.17 | <0.001 |
| FAZ-CI (SCP) | | | <0.001 |
| FAZ-CI (DCP) | | | 0.002 |

FIG. 5

TABLE 5

| Parameters | Diagnostic accuracy (%) | | | |
|---|---|---|---|---|
| | Control vs. Disease | DR vs. SCR | NPDR Staging | SCR Staging |
| $BVT_s$ | 81.75 | 81.64 | 71.26 | 89.15 |
| $BVC_s$ | 79.88 | 73.59 | 78.51 | 71.92 |
| $VPI_s$ | 76.49 | 76.83 | 78.39 | 65.46 |
| $BVD_{sc1}$ | 72.11 | 53.14 | 63.02 | 55.19 |
| $BVD_{sc2}$ | 80.02 | 77.98 | 75.83 | 74.98 |
| $BVD_{sc3}$ | 89.01 | 83.49 | 82.67 | 83.67 |
| $BVD_{Dc1}$ | 69.35 | 52.17 | 64.30 | 58.02 |
| $BVD_{Dc2}$ | 78.53 | 75.83 | 78.54 | 76.20 |
| $BVD_{Dc3}$ | 80.69 | 70.28 | 77.13 | 65.59 |
| $FAZ-A_s$ | 91.67 | 83.66 | 85.02 | 78.84 |
| $FAZ-A_D$ | 88.48 | 80.09 | 80.46 | 76.11 |
| $FAZ-Cl_s$ | 88.74 | 81.57 | 79.34 | 80.95 |
| $FAZ-Cl_D$ | 89.05 | 82.65 | 78.95 | 75.69 |
| Optimal feature combination | 97.45 | 94.32 | 89.60 | 93.11 |

* Superscript S and D denote SCP and DCP respectively. In case of BVD, C1-C3 denote circular area 1, 2 and 3 respectively as shown in figure 5.

FIG. 6

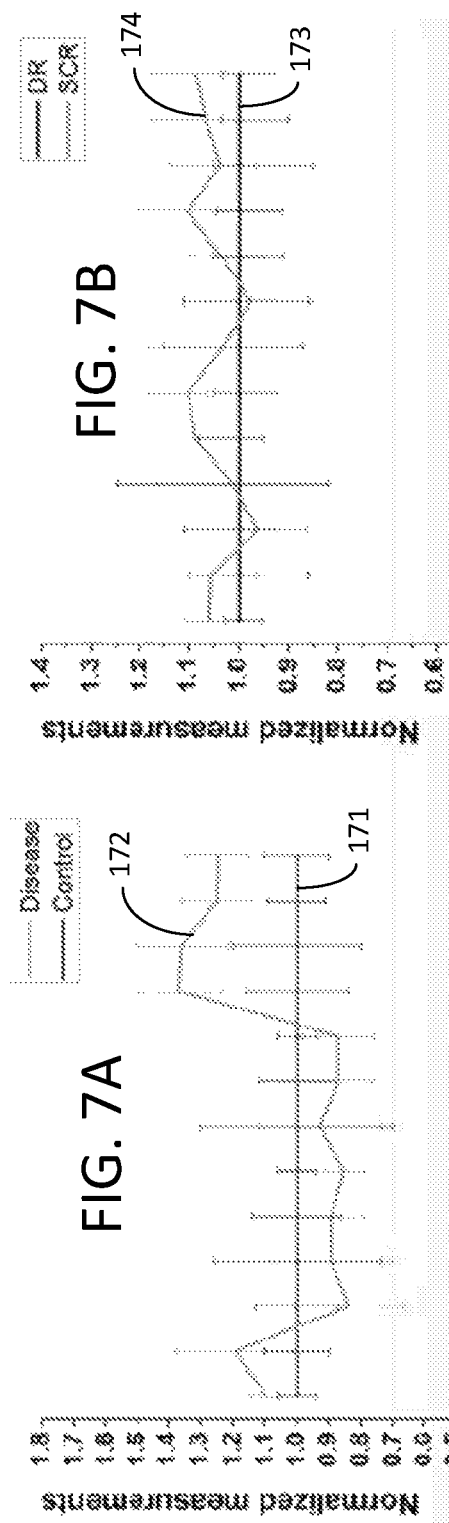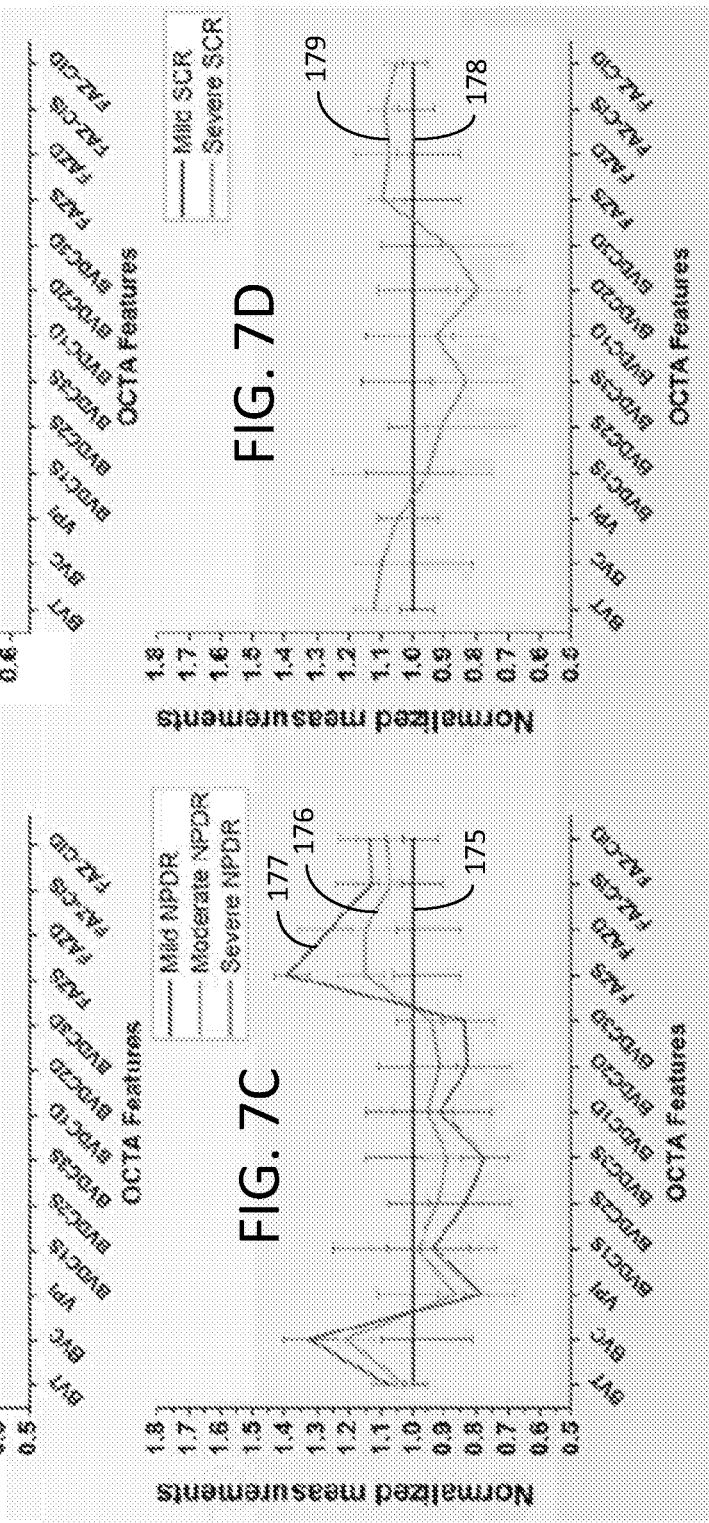

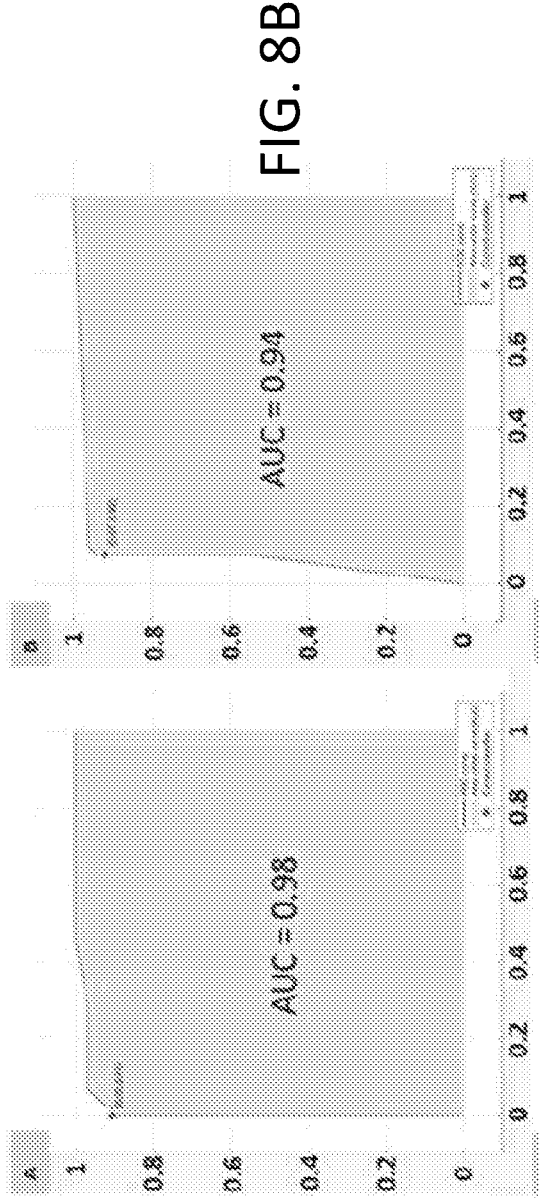
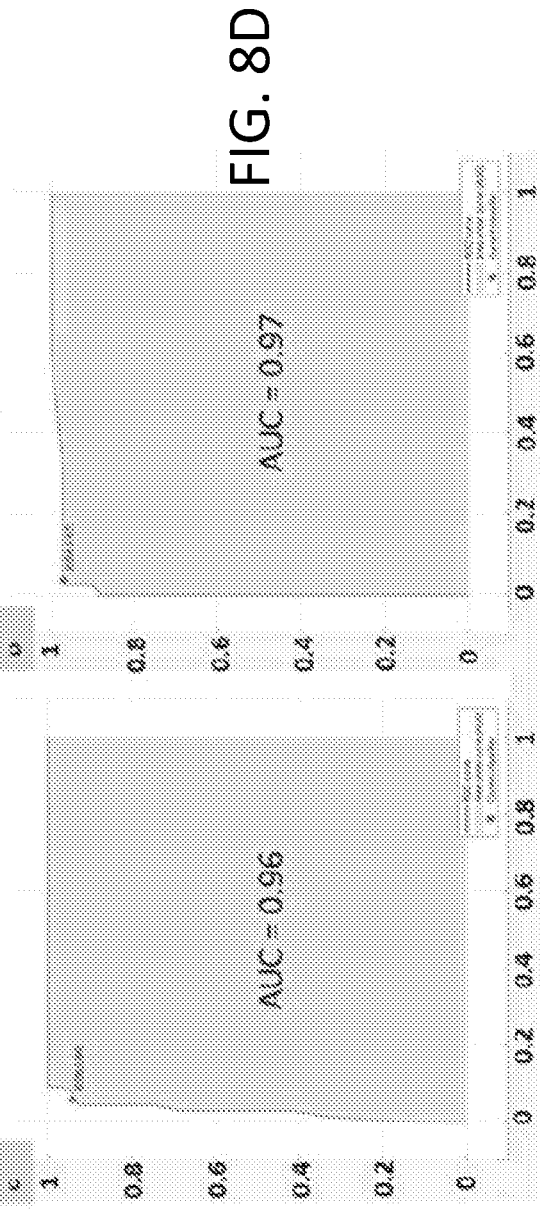
FIG. 8A  FIG. 8B  FIG. 8C  FIG. 8D

TABLE 6

| Parameters | Classification performance | | |
|---|---|---|---|
| | Area under the ROC curve, AUC | Sensitivity (%) | Specificity (%) |
| Control vs. Disease | 0.98 | 97.84 | 96.88 |
| DR vs. SCR | 0.94 | 95.01 | 92.25 |
| NPDR Staging | 0.96 | 92.18 | 86.43 |
| SCR Staging | 0.97 | 93.19 | 91.60 |

FIG. 9

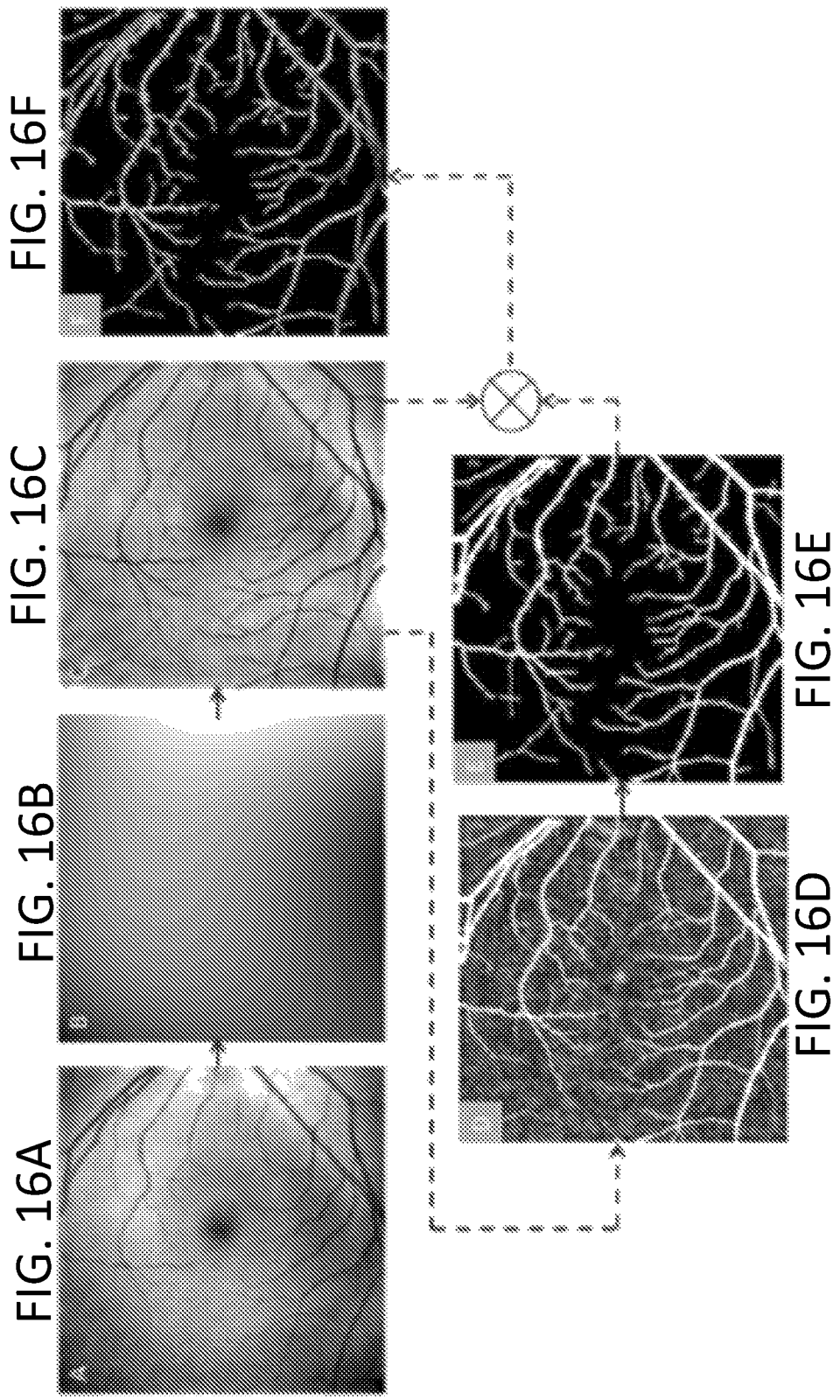

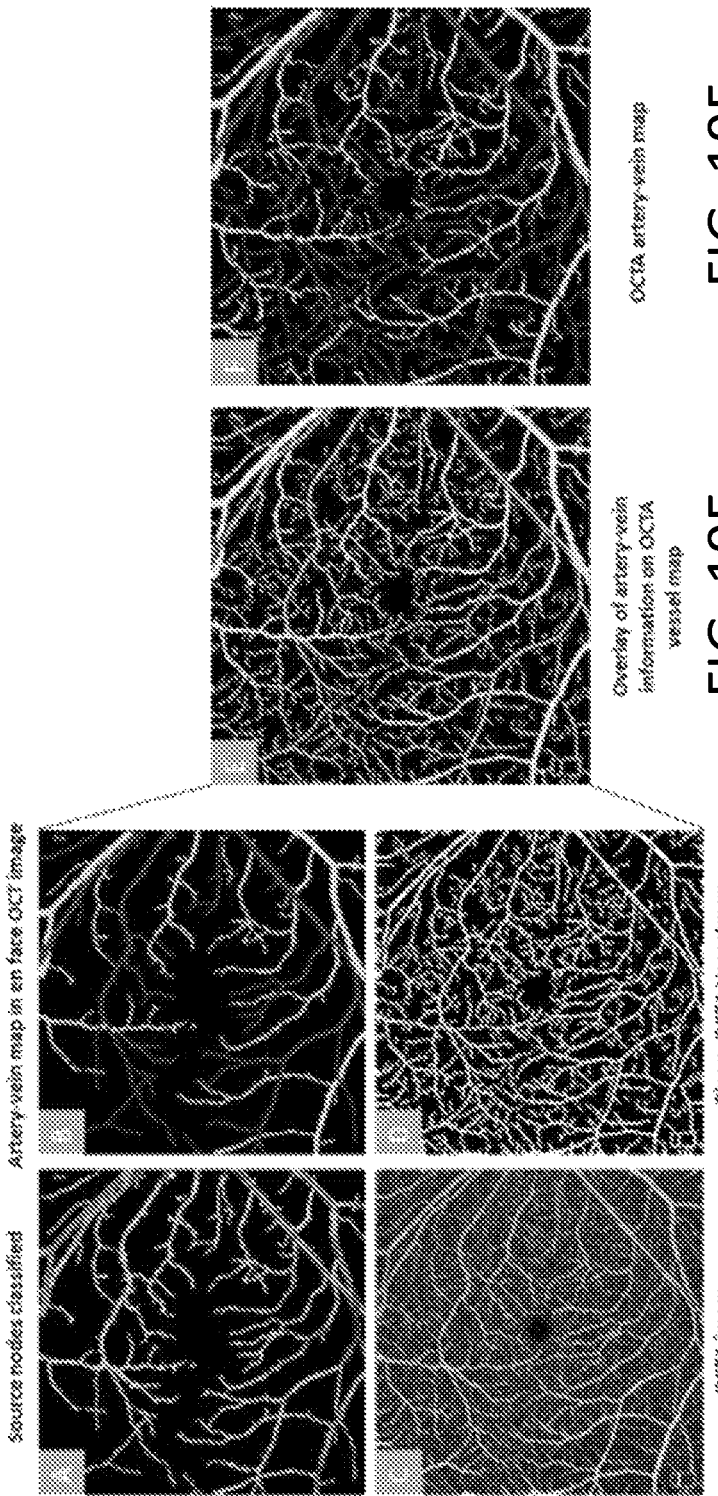
FIG. 19A Source nodes classified
FIG. 19B Artery-vein map in en face OCT image
FIG. 19C OCTA image
FIG. 19D Binary OCTA vessel map
FIG. 19E Overlay of artery-vein information on OCTA vessel map
FIG. 19F OCTA artery-vein map

TABLE 7

| Performance Measure | Source nodes | | | Whole vessel map | | |
|---|---|---|---|---|---|---|
| | Arteries | Veins | All vessels | Arteries | Veins | All vessels |
| Sensitivity (%) | 97.16 | 96.64 | 96.86 | 97.07 | 96.52 | 96.79 |
| Specificity (%) | 95.73 | 96.15 | 95.94 | 95.29 | 96.14 | 95.72 |
| Classification Accuracy (%) | 96.89 | 96.59 | 96.74 | 96.81 | 96.33 | 96.57 |
| AUC (%) | 98.29 | 98.03 | 98.21 | 98.16 | 97.93 | 98.00 |
| Classification Error rate (%) | 3.11 | 3.41 | 3.26 | 3.19 | 3.67 | 3.43 |

FIG. 21

TABLE 8

| Performance Measure | Arteries | Veins | All vessels |
|---|---|---|---|
| Sensitivity (%) | 97.02 | 96.3 | 96.66 |
| Specificity (%) | 94.98 | 95.01 | 95.00 |
| Classification Accuracy (%) | 96.77 | 96.25 | 96.51 |
| AUC (%) | 95.47 | 96.18 | 95.83 |
| Classification Error rate (%) | 3.23 | 3.75 | 3.49 |

FIG. 22

SUPERVISED MACHINE LEARNING BASED MULTI-TASK ARTIFICIAL INTELLIGENCE CLASSIFICATION OF RETINOPATHIES

CROSS-REFERENCE TO RELATED APPLICATIONS

This application is a national stage entry pursuant to 35 U.S.C. § 371 of Patent Cooperation Treaty (PCT) international application No. PCT/US2020/022774, filed on Mar. 13, 2020, which claims priority to, and the benefit of the filing date of, U.S. provisional application Nos. 62/840,061 and 62/818,065, filed on Apr. 29, 2019 and Mar. 13, 2019, respectively, entitled "SUPERVISED MACHINE LEARNING BASED MULTI-TASK ARTIFICIAL INTELLIGENCE CLASSIFICATION OF RETINOPATHIES" and "OCT FEATURE ANALYSIS GUIDED ARTERY-VEIN DIFFERENTIATION IN OCTA," respectively, all of which are incorporated herein by reference in their entireties.

STATEMENT OF GOVERNMENTAL INTEREST

The present invention was made under NIH grants R01 EY023522 and R01 EY024628. The government has certain rights in this invention.

TECHNICAL FIELD

The present disclosure is directed to predicting retinopathies, and more particularly, to using a machine learning-based, artificial intelligence (AI) system to predict retinopathies based on retinal features contained in optical coherence tomography angiography (OCTA) image data.

BACKGROUND

AI classification holds promise as a novel and affordable screening tool for clinical management of ocular diseases. Rural and underserved areas, which suffer from lack of access to experienced ophthalmologists, may particularly benefit from this technology. Machine learning-based AI technology has garnered increasing interest in medical applications over the past few years. AI-based diagnosis tools are designed to mimic the perception of the human brain for information processing and making objective decisions. Recent studies have demonstrated AI applications in detecting retinal disease progression, identifying malignant or benign melanoma, and classifying pulmonary tuberculosis. In ophthalmic research, application of AI technology has led to excellent diagnostic accuracy for several ocular conditions such as diabetic retinopathy (DR), age related macular degeneration (AMD), and sickle cell retinopathy (SCR).

In the current clinical setting, mass screening programs for common ocular conditions such as DR or SCR are heavily dependent upon experienced physicians to examine and evaluate retinal photographs. This process is time consuming and expensive, making it difficult to scale up to incorporate the millions of individuals, who harbor systematic diseases which are prone to affect the retina. Patients with early onset of retinopathies such as DR or SCR are initially asymptomatic, yet require monitoring to ensure prompt medical interventions to prevent vision losses. However, it is not feasible to screen 65 million people in the USA over the age of 50 years, to identify for individuals with signs of early retinopathy (AMD, DR or other disease). A diagnostic tool with capability for multiple-disease differentiation would have tremendous potential to advance mass-level screening of eye diseases.

To date, most of the reported studies of AI diagnostic systems in literature are based on color fundus photography. Fundus photography is one of the most common clinical imaging modalities and has been widely used in evaluating retinal abnormalities. Supervised and unsupervised machine learning based diagnostic systems using fundus images have been developed by researchers for staging of individual retinopathies as well as to identify multiple ocular diseases. However, these demonstrated AI-based diagnostic tools generally face two major challenges. First, fundus images provide limited resolution and retinal vascular information, limiting its capability to quantify subtle micro-vascular distortions near the foveal area and in different retinal layers. Thus, diagnostic systems using supervised machine learning algorithms suffer from low-performing quantitative feature analysis and concurrently low diagnostic accuracy. Second, systems using unsupervised or deep machine learning require a large and well documented database (ranging from 100,000 to millions) for training and optimizing convolutional neural networks. Even if an AI system is successfully trained, the intrinsic variance among different databases from multiple imaging centers makes it extremely difficult to provide robust accuracy metrics.

A need exists for a system that overcomes these challenges.

SUMMARY

An AI system is disclosed herein that classifies retinal features and predicts, based on the classified retinal features, one or more retinopathies. The AI system comprises a processor configured to perform a machine learning algorithm and a memory device in communication with the processor. The processor is configured to perform a machine learning algorithm that trains a classifier model to identify, classify and predict retinal features contained in OCTA training data. After the classifier model has been trained, the processor uses the classifier model to process acquired OCTA data acquired by an image acquisition system to classify retinal features contained in the acquired OCTA data and to predict, based on the classified retinal features contained in the acquired OCTA data, whether the acquired OCTA data is indicative of at least one of a plurality of retinopathies.

In accordance with a representative embodiment, when the processor uses the classifier model to predict, based on the classified retinal features contained in the acquired OCTA data, whether the acquired OCTA data is indicative of at least one of a plurality of retinopathies, the processor also predicts a respective stage of development of said one or more retinopathies ranging from non-proliferative stages to proliferative stages of development.

In accordance with a representative embodiment, the classifier model utilizes a hierarchical backward elimination technique to identify a plurality of combinations of retinal features to be used in the training process to train the classifier model to identify and classify retinal features contained in the acquired OCTA data.

In accordance with a representative embodiment, the process of training the classifier model comprises configuring the classifier model to identify a plurality of combinations of retinal features contained in the OCTA training data and to associate each of the plurality of combinations of retinal features with a respective retinopathy.

In accordance with a representative embodiment, the process of training the classifier model comprises configuring the classifier model to identify a plurality of combinations of retinal features contained in the OCTA training data and to associate one or more of the plurality of combinations of retinal features with a respective stage of development of the respective retinopathy.

In accordance with a representative embodiment, the process of using the classifier model comprises identifying at least one of the combinations of retinal features contained in the acquired OCTA data and predicting, based on the identification of said at least one of the combinations of retinal features contained in the acquired OCTA data, whether the acquired OCTA data is indicative of at least one of a plurality of retinopathies and a respective stage of development of the respective retinopathy.

In accordance with a representative embodiment, each combination of retinal features includes two or more of: blood vessel tortuosity (BVT), blood vascular caliber (BVC), vessel perimeter index (VPI), blood vessel density (BVD), foveal avascular zone (FAZ) area (FAZ-A), and FAZ contour irregularity (FAZ-CI).

In accordance with a representative embodiment, the process performed by the machine learning algorithm further comprises retraining the classifier model to identify at least one different combination of retinal features based at least in part on the prediction of whether the acquired OCTA data is indicative of at least one of a plurality of retinopathies.

In accordance with a representative embodiment, when the processor uses the classifier model to predict, based on the classified retinal features contained in the acquired OCTA data, whether the acquired OCTA data is indicative of at least one of a plurality of retinopathies and a respective stage of development, the processor performs multi-layer hierarchical classification comprising: normal versus disease classification; inter-disease classification; and stage classification.

In accordance with a representative embodiment, the inter-disease classification includes at least DR versus SCR classification.

In accordance with a representative embodiment, the normal versus disease classification includes at least normal versus DR classification and normal versus SCR classification.

In accordance with a representative embodiment, the stage classification includes at least mild, moderate and severe non-proliferative DR (NPDR) stage classification and mild and severe SCR stage classification.

In accordance with a representative embodiment, during the process of training the classifier model, the machine learning algorithm comprises a hierarchical backward elimination algorithm constructed (or configured) to identify the combinations of retinal features that achieve the best prediction accuracy, selects the identified combinations of retinal features and configures the classifier model to perform normal versus disease classification, inter-disease classification; and the stage classification based on combinations of retinal features contained in the acquired OCTA data.

In accordance with a representative embodiment, the OCTA data comprises an OCTA artery-vein map obtained by:
generating an optical coherence tomography (OCT) artery-vein map from a spectrogram dataset;
generating an OCTA vessel map from the spectrogram dataset;
overlaying the OCT artery-vein map and the OCTA vessel map to generate an overlaid map; and
processing the overlaid map by using the OCT artery-vein map to guide artery-vein differentiation in the OCTA vessel map to generate the OCTA artery-vein map.

In accordance with a representative embodiment, a system for generating an OCTA artery-vein map is disclosed. The system comprises a processor configured to perform an OCTA artery-vein mapping algorithm that performs processes of:
processing a spectrogram dataset to generate an OCT artery-vein map;
processing the spectrogram dataset to obtain an OCTA vessel map;
overlaying the OCT artery-vein map and the OCTA vessel map to generate an overlaid map; and
processing the overlaid map by using the OCT artery-vein map to guide artery-vein differentiation in the OCTA vessel map to generate the OCTA artery-vein map.

In accordance with a representative embodiment, the spectrogram dataset comprises an en face OCT image that is processed to generate the OCT artery-vein map.

In accordance with a representative embodiment, the spectrogram dataset is obtained by an image acquisition system that uses a light source that emits oxygen sensitive wavelengths.

In accordance with a representative embodiment, the emitted oxygen sensitive wavelengths include near infrared (NIR) wavelengths.

In accordance with a representative embodiment, processing the en face OCT image to generate the OCT artery-vein map comprises:
performing intensity normalization of the en face OCT image to generate an intensity-normalized en face OCT image;
filtering the intensity-normalized en face OCT image to generate a blood vessel mask;
multiplying the blood vessel mask by the intensity-normalized en face OCT image to generate a segmented blood vessel map;
in a portion of the segmented blood vessel map, identifying source nodes of blood vessels in the segmented blood vessel map and modifying the segmented blood vessel map to include indicia identifying the source nodes of blood vessels;
extracting features contained in the portion of the segmented blood vessel map, performing feature analysis to classify the extracted features and modifying the segmented blood vessel map to include indicia identifying source node segments of the blood vessel map as artery or vein;
finalizing the OCT artery-vein map by performing a blood vessel tracking algorithm that tracks blood vessels connected to the identified source nodes, identifies blood vessels that are connected to the identified source nodes as artery or vein throughout the segmented blood vessel map, and modifies the segmented blood vessel map to include indicia identifying the tracked blood vessels as artery or vein.

In accordance with a representative embodiment, the spectrogram dataset comprises an OCTA image that is processed to generate the OCTA vessel map, and processing the OCTA image to generate the OCTA vessel map comprises:
performing a filtering the OCTA image with a filter algorithm to enhance vascular flow information contained in the OCTA image; and performing an adaptive thresholding algorithm on the filtered OCTA image to remove noise and structures that are not capable of being tracked by a blood vessel tracking algorithms.

These and other features and advantages will become apparent from the following description, drawings and claims.

BRIEF DESCRIPTION OF THE DRAWINGS

FIG. 2 is a table containing patient demographic data for patients used in a study to test and validate the AI system shown in FIG. 1.

FIGS. 3-5 show tables summarizing quantitative univariate analysis of OCTA features for comparing control vs. DR vs. SCR, NPDR stages and SCR stages.

FIG. 6 shows a table comparing the diagnostic accuracy for various retinal features measured by the AI system shown in FIG. 1 using a backward elimination algorithm for feature selection.

FIGS. 7A-7D are plots of OCTA features vs. normalized measurements for different cohorts, namely, change in disease group (DR and SCR) compared to control, change in SCR compared to DR, change in moderate and severe NPDR compared to mild NPDR, and change in severe SCR compared to mild SCR.

FIGS. 8A-8D show ROC curves illustrating classification performance of the classifier model shown in FIG. 1 using selected combinations of retinal features for control vs disease classification, DR vs. SCR classification, NPDR staging and SCR staging, respectively.

FIG. 9 shows a table that lists performance metrics for an embodiment of the AI system shown in FIG. 1.

FIGS. 16A-16F are images illustrating OCT normalization and vessel segmentation.

FIG. 19A shows the en face OCT vessel map with the source nodes classified.

FIG. 19B shows the en face OCT vessel map with the arteries and veins classified.

FIG. 19C shows the original captured OCTA image.

FIG. 19D shows an OCTA vessel map.

FIG. 19E shows an overlaid map generated by overlaying the en face OCT artery-vein map shown in FIG. 19B with the OCTA vessel map shown in FIG. 19D.

FIG. 19F shows an OCTA artery-vein map generated using the overlaid map shown in FIG. 19E as a guide.

FIGS. 21 and 22 show tables of the performances of artery-vein classification in OCT and OCTA in accordance with an embodiment.

DETAILED DESCRIPTION

Figure 1:
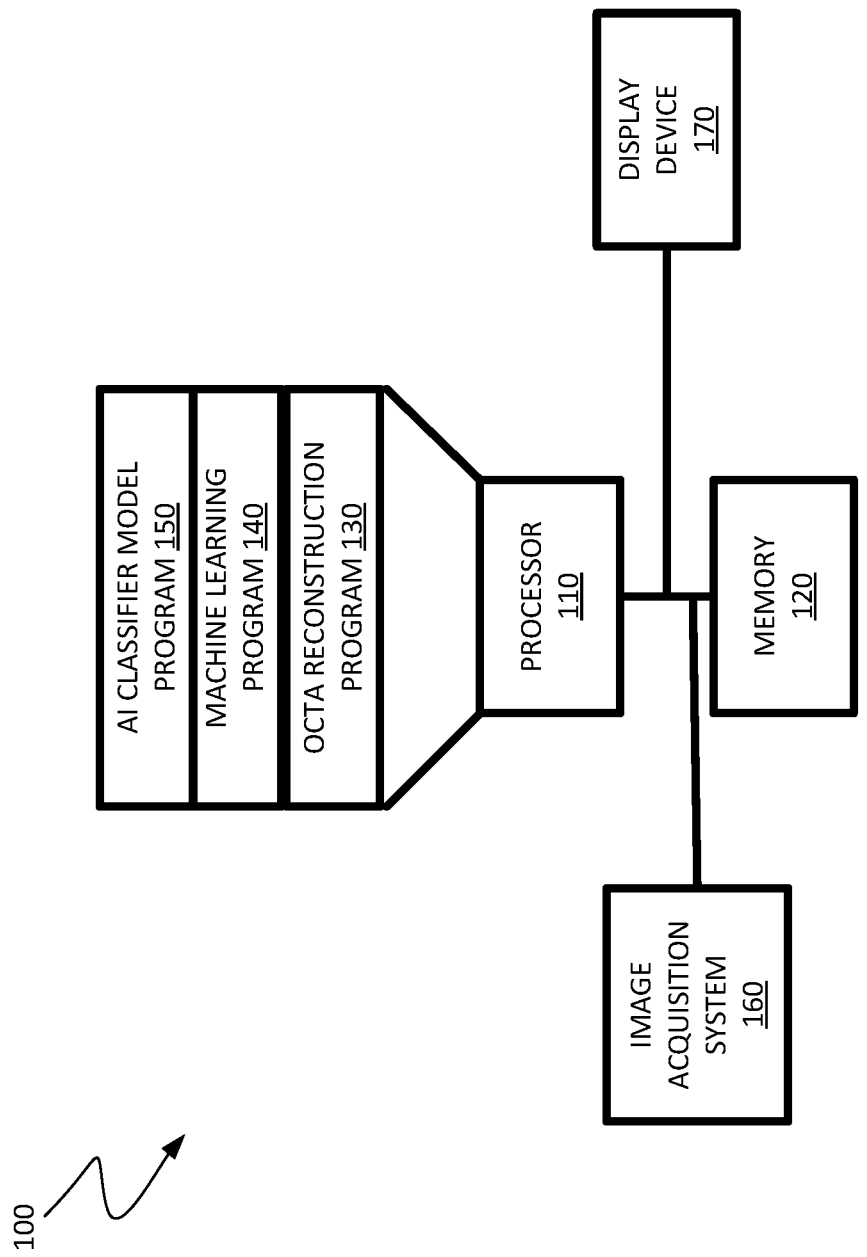
FIG. 1 is a block diagram of the AI system in accordance with a representative embodiment.

Quantitative OCTA imaging provides excellent capability to identify subtle vascular distortions, which are useful for classifying retinovascular diseases. In accordance with the principles herein, an AI system for differentiation and classification of multiple eye diseases is set forth. As a solution to overcome the aforementioned challenges associated with current AI-based systems that utilize color fundus photography, the AI system disclosed herein uses machine learning to classify retinal features contained in OCTA data acquired by a data acquisition system to predict one or more retinopathies based on the classification of retinal features. The AI system comprises a processor configured to run a classifier model comprising a machine learning algorithm and a memory device that stores the classifier model, OCTA training data and acquired OCTA data. The machine learning algorithm performs a process that trains the classifier model to classify retinal features contained in OCTA training data. After the classifier model has been trained, the machine learning algorithm uses the classifier model to process acquired OCTA data to classify retinal features contained in the acquired OCTA data and to predict, based on the classified retinal features, whether the acquired OCTA data is indicative of at least one of a plurality of retinopathies.

In accordance with a representative embodiment, the processor performing the machine learning algorithm also predicts a respective stage of development of the predicted retinopathy ranging from an early stage of development to a fully progressed stage of development. Normally, retinal diseases have two primary stages or ranges of stages: early stages and more progressed stages. The early stages, also known as non-proliferative stages, include mild, moderate and severe stages. The more progressed stages are proliferative stages where there is hemorrhage and vision could be impaired. In the proliferative stages, the treatment plan needs to be more aggressive and anti-vascular endothelial growth factor (vegf) injections are required to stop neovascularization.

In accordance with a representative embodiment, in addition to the processor of the AI system being configured to predict retinopathies, the processor is also configured to predict staging, i.e., to perform classification for both non-proliferative (early detection) and proliferative (detection of progression into later stages). The terms mild, moderate and severe may not be universal for all types of retinal disease (mostly used in diabetic retinopathy). For example, for AMD, the early and late stages are classified as dry and wet AMD, respectively, where dry corresponds to non-proliferative and wet corresponds to proliferative. For clarity, the term non-proliferative as used herein denotes mild, moderate and severe stages and the term proliferative, as used herein, denotes the more progressed stages where there is hemorrhage and vision could be impaired.

In accordance with a representative embodiment, the OCTA data comprises an OCTA artery-vein map obtained by performing the steps of: generating an OCT artery-vein map from a spectrogram dataset, generating an OCTA vessel map from the spectrogram dataset, overlaying the OCT artery-vein map and the OCTA vessel map to generate an overlaid map, and processing the overlaid map by using the OCR artery-vein map to guide artery-vein differentiation in the OCTA vessel map to generate the OCTA artery-vein map. In accordance with this representative embodiment, the processor of the AI system can be configured to perform an OCTA artery-vein mapping algorithm that performs the processes of processing the spectrogram dataset to generate the OCT artery-vein map, processing the same spectrogram dataset to obtain an OCTA vessel map, overlaying the OCT artery-vein map and the OCTA vessel map to generate the overlaid map, and processing the overlaid map by using the OCR artery-vein map to guide artery-vein differentiation in the OCTA vessel map to generate the OCTA artery-vein map.

In accordance with a representative embodiment, the AI system can be a supervised machine learning system and the classifier model is a support vector machine (SVM) classifier model trained with quantitative OCTA features to allow the AI system to be used for multi-task AI classification of retinopathies and staging. In accordance with inventive principles and concepts described herein, it has been determined that retinopathies such as DR and SCR show different effects on OCTA features, and thus that quantitative OCTA analysis can be employed for multiple-task classification of different retinopathies and stages. The term "multi-task" OCTA classification, as used herein, denotes using the AI system to classify multiple OCTA features in order to differentiate between multiple retinopathies at multiple stages of progression of the retinopathies.

In the present disclosure, the feasibility of using quantitative OCTA features for machine leaning-based, multi-task AI screening of different retinopathies is demonstrated. For easy comparison with recent studies conducted by the inventors, DR and SCR were selected as the two diseases for technical validation of the AI screening methodology disclosed herein. It should be noted, however, that the inventive principles and concepts are not limited to screening for DR and SCR, but can be used to screen other retinopathies. Persons of skill in the art will understand, in view of the description provided herein, how the inventive principles and concepts can be applied to screen other types of retinopathies.

In accordance with inventive concepts and principles disclosed herein, it has been determined that because OCTA provides excellent capability for depth-resolved visualization of retinal vascular plexuses, quantitative OCTA can be employed for AI screening of multiple retinopathies. Although the comparatively smaller data size of OCTA presently limits deep-learning-based strategies, the sensitivity of OCTA features to detect onset and progression of different retinopathies makes it readily useful for supervised AI-based screening. Recent studies have established several quantitative OCTA features correlated with subtle pathological and microvascular distortions in the retina. OCTA features such as blood vessel tortuosity (BVT), blood vascular caliber (BVC), vessel perimeter index (VPI), blood vessel density (BVD), foveal avascular zone (FAZ) area (FAZ-A), and FAZ contour irregularity (FAZ-CI) have also been validated for objective classification and staging of DR and SCR, individually. In accordance with the inventive principles and concepts disclosed herein, it has been determined that retinopathies such as DR and SCR show different effects on OCTA features, and thus quantitative OCTA analysis can be employed for multiple-task classification to differentiate retinopathies and stages, as discussed below in detail.

In the following detailed description, for purposes of explanation and not limitation, exemplary, or representative, embodiments disclosing specific details are set forth in order to provide a thorough understanding of an embodiment according to the present teachings. However, it will be apparent to one having ordinary skill in the art having the benefit of the present disclosure that other embodiments according to the present teachings that depart from the specific details disclosed herein remain within the scope of the appended claims. Moreover, descriptions of well-known apparatuses and methods may be omitted so as to not obscure the description of the example embodiments. Such methods and apparatuses are clearly within the scope of the present teachings.

The terminology used herein is for purposes of describing particular embodiments only and is not intended to be limiting. The defined terms are in addition to the technical and scientific meanings of the defined terms as commonly understood and accepted in the technical field of the present teachings.

As used in the specification and appended claims, the terms "a," "an," and "the" include both singular and plural referents, unless the context clearly dictates otherwise. Thus, for example, "a device" includes one device and plural devices.

Relative terms may be used to describe the various elements' relationships to one another, as illustrated in the accompanying drawings. These relative terms are intended to encompass different orientations of the device and/or elements in addition to the orientation depicted in the drawings.

It will be understood that when an element is referred to as being "connected to" or "coupled to" or "electrically coupled to" another element, it can be directly connected or coupled, or intervening elements may be present.

The term "memory" or "memory device", as those terms are used herein, are intended to denote a non-transitory computer-readable storage medium that is capable of storing computer instructions, or computer code, for execution by one or more processors. References herein to "memory" or "memory device" should be interpreted as one or more memories or memory devices. The memory may, for example, be multiple memories within the same computer system. The memory may also be multiple memories distributed amongst multiple computer systems or computing devices.

A "processor", as that term is used herein encompasses an electronic component that is able to execute a computer program or executable computer instructions. References herein to a computer comprising "a processor" should be interpreted as one or more processors or processing cores. The processor may for instance be a multi-core processor. A processor may also refer to a collection of processors within a single computer system or distributed amongst multiple computer systems. The term "computer" should also be interpreted as possibly referring to a collection or network of computers or computing devices, each comprising a processor or processors. Instructions of a computer program can be performed by multiple processors that may be within the same computer or that may be distributed across multiple computers.

Exemplary, or representative, embodiments will now be described with reference to the figures, in which like reference numerals represent like components, elements or features. It should be noted that features, elements or components in the figures are not intended to be drawn to scale, emphasis being placed instead on demonstrating inventive principles and concepts.

FIG. 1 is a block diagram of the AI system 100 in accordance with a representative embodiment. A processor 110 of the AI system 100 is configured to perform an OCTA reconstruction algorithm, an AI classifier model algorithm, and a machine learning algorithm, each of which can be implemented in hardware, software, firmware, or a combination thereof. Because these algorithms are typically computer programs implemented in software, firmware, or a combination thereof, the algorithms are described herein and shown in FIG. 1 as an OCTA reconstruction program 130, a machine learning program 140 and an AI classifier model program 150. It should be noted that although the machine learning program 140 and the AI classifier model program 150 are shown as being separate programs, they may be implemented as a single computer program. The OCTA reconstruction program 130 may also be integrated with the machine learning program 140 and/or the AI classifier model program 150.

The machine learning program 140 trains the classifier model program 150 to classify retinal features. The manner in which training is performed is described below in more detail. Once trained, the classifier model program 150 analyzes OCTA images captured by a data acquisition system 160 of the AI system 100 to identify and classify retinal features contained in the images. Based on the classification of the retinal features, the machine learning program predicts one or more retinopathies and the corresponding stage development of the classified retinopathies. A memory device 120 of the AI system is used for storing the computer instructions comprising the programs 130, 140 and 150 and also comprises a database for storing OCTA data, retinal features and combinations of retinal features as well as relationships associating retinal features or combinations of retinal features with the associated retinopathies and stages. The AI system 100 typically includes a display device 170 for displaying information, such as results of classification of retinopathies, staging and images captured by the data acquisition system 160.

In accordance with a representative embodiment, the AI classifier model program 150 is a support vector machine (SVM) classifier model program that utilizes a hierarchical backward elimination algorithm to identify optimal retinal feature combinations for achieving the best diagnostic accuracy with the most efficient classification performance. In accordance with a representative embodiment, the AI system 100 functions as a screening tool that performs multi-layer hierarchical tasks to perform 1) normal vs. disease classification, 2) inter-disease classification (e.g., DR vs. SCR), and 3) staging (e.g., mild, moderate and severe non-proliferative DR (NPDR) and (mild and severe SCR). The performance of the AI system 100 has been quantitatively validated with manually labeled ground truth using sensitivity, specificity and accuracy metrics along with graphical metrics, i.e., receiver operation characteristics (ROC) curves.

An exemplary OCTA image database study conducted by the inventors in accordance with the inventive principles and concepts disclosed herein included 115 images from 60 DR patients (20 mild, 20 medium and 20 severe NPDR), 90 images from 48 SCR patients (30 stage II mild and 18 stage III severe SCR), and 40 images from 20 control patients. Patient demographic data is shown in Table 1 shown in FIG. 2. There were no statistical significances in age and sex distribution among the control, DR and SCR groups. (ANOVA, $P=0.14$; chi-square test, $P=0.11$ and $P=0.32$, respectively). For DR, no significance in hypertension or insulin dependency between stages of disease groups was observed.

Optimal Feature Selection Using Backward Elimination

The hierarchical backward elimination algorithm of the machine learning program 140 was employed to select a suitable, and preferably optimal, combination of features for the multi-task OCTA classification. A summary of the quantitative univariate analysis of the OCTA features is provided in Tables 2-4 shown in FIGS. 3-5, respectively, for comparing control vs. DR vs. SCR, NPDR stages and SCR stages, respectively. In general, BVT, BVC and FAZ parameters increased with disease onset and progression whereas BVD and VPI decreased with disease onset and progression. The comparison of the diagnostic accuracy for each feature measured in the backward elimination algorithm is provided in Table 5 shown in FIG. 6.

FIGS. 7A-7D provide further support to the results shown in Table 5. FIGS. 7A-7D are plots of OCTA features vs. normalized measurements for different cohorts, namely, change in disease group (DR and SCR) compared to control (FIG. 7A), change in SCR compared to DR (FIG. 7B), change in moderate and severe NPDR compared to mild NPDR (FIG. 7C), and change in severe SCR compared to mild SCR (FIG. 7D). The error bars shown in FIGS. 7A-7D represent standard deviation. In FIG. 7A, the plots 171 and 172 represent the control group and the disease group, respectively. In FIG. 7B, the plots 173 and 174 represent the DR group and the SCR group, respectively. In FIG. 7C, the plots 175, 176 and 177 represent the mild NPDR group, the moderate NPDR group and the severe NPDR group, respectively. In FIG. 7D, the plots 178 and 179 represent the mild SCR group and the severe SCR group, respectively.

Relative changes of OCTA features among different groups is evident from the plots shown in FIGS. 7A-7D. Each plot shown in FIGS. 7A-7D corresponds to four classification tasks. The backward elimination algorithm initially started with all OCTA features and eliminated OCTA features one by one based on the prediction accuracy of the fitted regression model. The feature selection method identified a suitable, and possibly optimal, feature combination for each classification task as follows: perifoveal $BVD_{SC3}$ (SCP, circular area: >4 mm), $FAZ-A_S$ (SCP) and $FAZ-CI_D$ (DCP) for control vs. disease classification; $BVT_S$ (SCP), $BVD_{SC3}$, $FAZ-A_S$, and $FAZ-CI_D$ for DR vs. SCR classification; $BVD_{SC3}$ and $FAZ-A_S$ for NPDR staging; and $BVT_S$, $BVD_{SC3}$, and $FAZ-CI_S$ (SCP) for SCR staging. Table 5 (FIG. 6) shows that the individual accuracy of the optimal features in each of the classification tasks were highest compared to the other features and the model fitted with the combination of these optimal features provided the best diagnostic accuracy. Also, from FIGS. 7A-7D it can be seen that the relative changes in each cohort can only be observed in the chosen optimal OCTA features.

Multi-Task OCTA Classification

As indicated above, in accordance with a representative embodiment, the classifier model 150 (FIG. 1) is an SVM classifier model that performs the classification tasks in a hierarchical backward elimination manner. To evaluate the diagnostic performance in each step or task, the sensitivity and specificity tasks were measured. For each task, the ROC curves were also drawn (FIGS. 8A-8D) and AUCs were calculated. FIGS. 8A-8D show ROC curves illustrating classification performances of the SVM classifier model 150 using the selected combinations of features for control vs disease classification, DR vs. SCR classification, NPDR staging and SCR staging, respectively.

At the first step of classification, the SVM classifier model 150 identifies diseased patients from control subjects with 97.84% sensitivity and 96.88% specificity (AUC 0.98, FIG. 8A). After identifying the diseased patients, the SVM classifier model 150 sorts them into two groups: DR and SCR with 95.01% sensitivity and 92.25% specificity (AUC 0.94, FIG. 8B). After sorting to the corresponding retinopathies, the SVM classifier model 150 conducts a condition staging classification: 92.18% sensitivity and 86.43% specificity for NPDR staging (mild vs. moderate vs. severe; AUC 0.96, FIG. 8C), and 93.19% sensitivity and 91.60% specificity for SCR staging (mild vs. severe; AUC 0.97, FIG. 8D). The sensitivity, specificity and AUC metrics are calculated for the SVM classifier model 150 trained with optimal feature combinations described above with reference to Tables 2-5 and FIGS. 7A-7D. Table 6 shown in FIG. 9 lists the performance metrics in further detail.

In accordance with the principles herein, an exemplary embodiment of a supervised machine learning based AI screening tool for multiple retinopathies using quantitative OCTA technology is set forth. In a hierarchical manner, this diagnostic tool can perform multiple-task classification to classify i) control vs. disease, ii) DR vs. SCR, iii) different stages of NPDR and SCR, using quantitative features extracted from OCTA images. OCTA images can provide visualization of subtle microvascular structures in intraretinal layers which permits a comprehensive quantitative analysis of pathological changes due to systematic retinal diseases such as DR and SCR.

Morphological distortions such as, for example, impaired capillary perfusion, vessel tortuosity and overall changes in foveal size and complexity, etc., were quantitatively measured and compared for identifying onset and progression of DR or SCR in diabetes and SCD patients, respectively. The SVM classifier model 150 demonstrated a robust diagnostic performance in all classification tasks. As indicated above, the classifier model 150 utilized a backward elimination algorithm for choosing an optimal combination of OCTA features for getting the best diagnostic performance with highest efficiency. Proper implementation of the AI system 100 in primary care centers would facilitate a quick and efficient way of screening and diagnosing vision impairment due to systematic diseases.

For any screening and diagnostic prediction system, sensitivity is a patient safety criterion. The major role of the AI system 100 is to identify patients prone to vision impairment due to retinopathies. In the control vs. disease classification task, 97.84% sensitivity of the system 100 represents the capability to identify individual eyes with retinopathies (DR and SCR) from a general pool of control, DR and SCR eyes, as shown in Table 6 shown in FIG. 9. Furthermore, the system 100 can identify patients with DR or SCR with 95.01% sensitivity, as shown in Table 6. This is crucial for screening purposes, as those patients should be referred to eye care specialists.

Similarly, specificity is also an important factor because it represents the capability of the system 100 to detect subjects that do not require referral to an eye care specialist. When the data pool equals millions of patients, this discriminatory capability is crucial for efficient clinical effectiveness in mass-screening. The system 100 demonstrates 96.88% specificity for control vs. disease (DR or SCR), which means the control subjects would rarely, if ever, be erroneously referred for treatment of retinopathies. Additionally, the system 100 demonstrated a 92.25% specificity in DR vs. SCR classification, as indicated in Table 6, which means that the patients with DR or SCR would rarely, if ever, be referred with an incorrect diagnosis. This is very important because certain advanced stages of a disease tend to progress faster than others and hence require more expedient evaluation and management upon referral. In mass-screening applications, the AI system 100 will be useful in identifying proper referral for patients with systematic diseases (e.g., diabetes or SCD) and avoid unnecessary referral for patients who do not need specialized care at that point in time.

An optimal combination of OCTA features can achieve maximum diagnostic accuracy for all classification tasks. As supported by results given in Table 5 shown in FIG. 6, it can be observed that, in all performance metrics, the classifier model 150 trained with the "optimal feature combination" (bottom row of Table 5) demonstrated better diagnostic proficiency compared to the model trained with individual features or combination of all features. The OCTA features analyzed in this study represent vascular and foveal distortions in retina due to retinopathy from both superficial and deep layers as well as localized circular regions in the retina (BVD). Out of all these OCTA features, the feature selection strategy identified the most sensitive features for each of the classification tasks to significantly distinguish different cohorts.

The high diagnostic accuracy of the classifier model 150 trained with optimal feature combination highlights the importance of selecting the most relevant features in automated classification. Few features that showed significance in the univariate analysis (FIGS. 3-5) were not selected in the final set of optimal features. This suggests a contrast between clinical applicability and overall difference of OCTA features among different patient groups.

In all of the classification tasks, it was observed that the most sensitive features also had low correlation amongst themselves. It was observed that only FAZ parameters had positive correlation with each other and that BVT and BVD both were not significantly correlated with FAZ parameters (Spearman's rank test, P>0.05), suggesting that all of the retinal features provided different pathological aspects of the diseased retina. Therefore, the four optimal features were objective for identifying distortions associated with DR or SCR and their feature combinations yielded strong classification performance.

Both BVD and FAZ parameters (FAZ-A and FAZ-CI) have been shown to be significant in identifying DR stages. BVT is also an established predictor for SCR progression. In two previous studies, the inventors previously demonstrated an SVM classifier model for automated staging of DR groups (mild, moderate, severe) and SCR groups (stage II and III). In the previous DR study, the most sensitive OCTA feature was observed to be BVD while for SCR, it was BVT and FAZ. These sensitive OCTA features are also selected to be included in the optimal feature set by the backward elimination technique in the current study discussed herein for different classification tasks. The current study, therefore, supports the previous findings and also demonstrates the clinical importance of identifying the most sensitive features for different retinopathies. Furthermore, the optimal features included measurements from both SCP and DCP. Previous OCTA studies, including the two previous studies by the inventors mentioned above, have suggested that the onset and progression of DR or SCR in diabetes or SCD patients affect both of the retinal layers. By choosing optimized features from SCP and DCP, the AI classifier model 150 ensured representation of layer specific distortions due to retinopathies.

For practical implementation of any AI-based tool in mass-screening at a clinical setting, a major challenge is the computation time required for overall feature extraction, optimization and diagnostic prediction. The AI system 100 that incorporated the SVM classifier model as the AI classifier model 150 required only a few seconds to extract features from each OCTA image. From the dataset of extracted features, the optimized features were chosen using the aforementioned backward elimination algorithm, which took slightly longer (done only one time) and depended on the size of the dataset. After the training of the SVM classifier model was completed, it took only a few seconds to classify the testing database used in this study. If new data is included for diagnosis prediction, it takes only a few seconds per OCTA image to use the trained model to classify control, DR or SCR eyes. It should be noted, however, that the inventive principles and concepts described herein are not limited with respect to the amount of time required to train the model 150 or the amount of time required for the system 100 to predict retinopathies and staging. The speed and efficiency with which the AI system 100 can operate allow users to view a real-time prediction on the display device 170 as soon as an OCTA image is captured in retina clinics. The diagnostic accuracy of the AI system 100 can be enhanced even further if the patient history or clinical information is integrated into the AI system 100.

In accordance with the representative embodiments discussed above, the AI system 100 is a supervised machine learning-based, multi-task OCTA classification tool that uses an optimal combination of quantitative OCTA features for objective classification of control, DR and SCR eyes with excellent diagnostic accuracy. Using the feature selection strategy discussed above, the classifier model 150 selected the following feature combinations: $BVD_{SC3}$, $FAZ-A_S$ and $FAZ-CI_D$ for control vs. disease classification; $BVT_S$, $BVD_{SC3}$, $FAZ-A_S$, and $FAZ-CI_D$ for DR vs. SCR classification; $BVD_{SC3}$ and $FAZ-A_S$ for staging of NPDR severity; and $BVT_S$, $BVD_{SC3}$, and $FAZ-CI_S$ for staging of SCR severity. The selected, and possibly optimal, feature combination directly correlates to the most significant morphological changes in retina for each classification task and provides the most effective classification performance with the least computational complexity. It should be noted, however, that the inventive principles and concepts are not limited to the particular feature combinations, as will be understood by those of skill in the art in view of the description provided herein. Although these feature combinations are believed to be optimal, additional studies may lead to the use of feature combinations that are slightly or altogether different from those described herein.

Figure 10A:
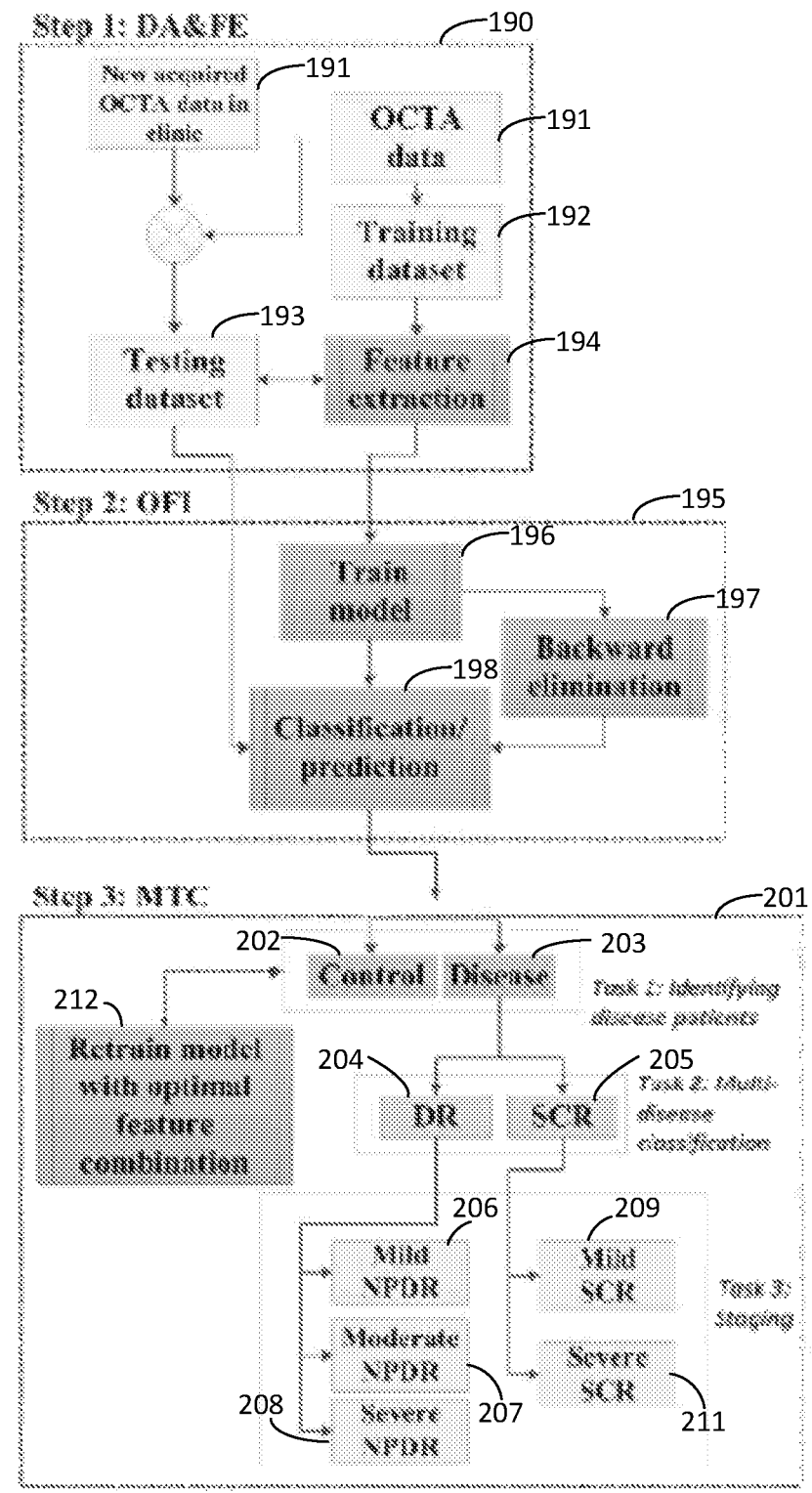
FIG. 10A is a flow diagram illustrating the method of AI-based classification performed by the AI system shown in FIG. 1 to predict retinopathies and the associated stages of progression in accordance with a representative embodiment.
Figure 10B:
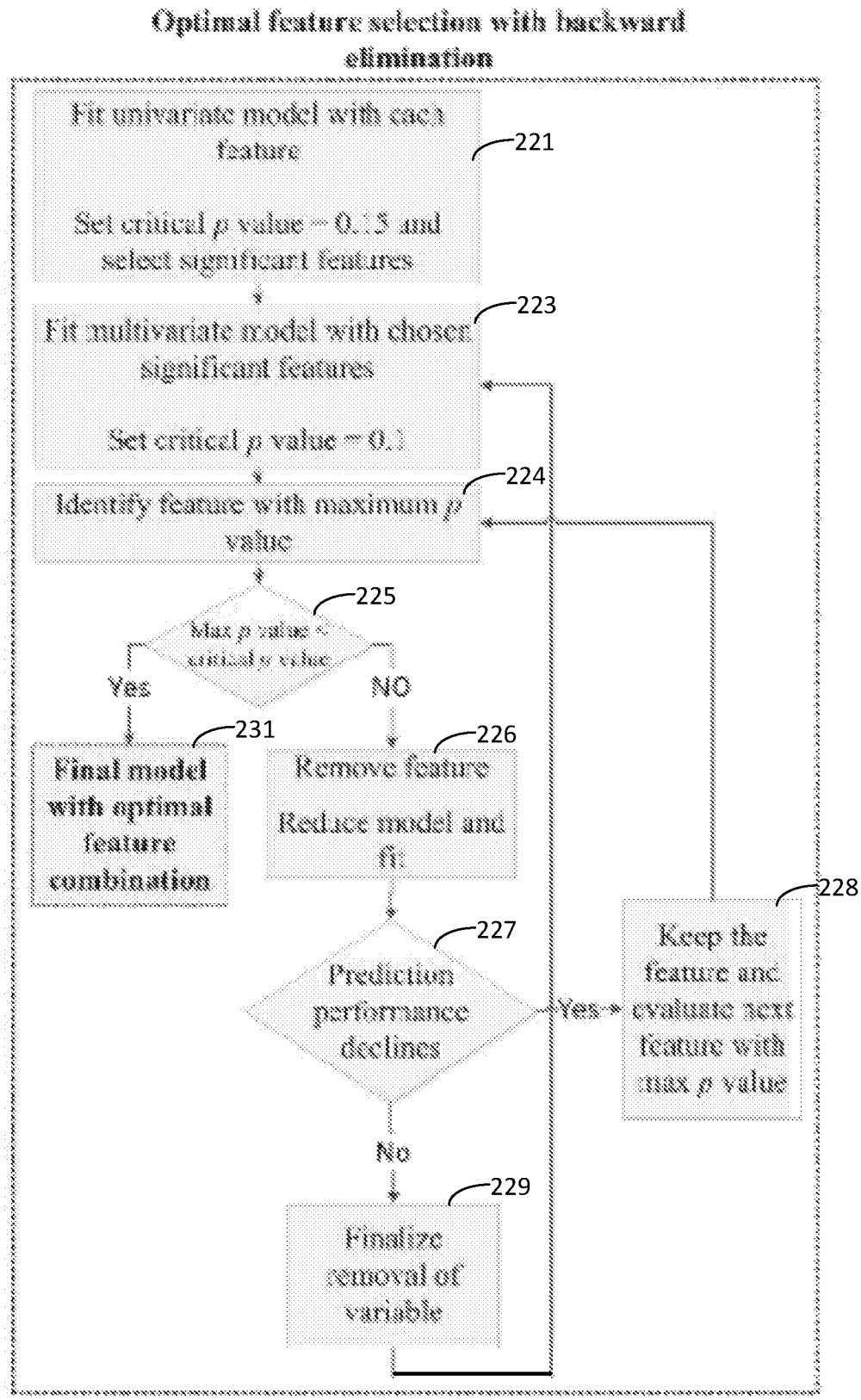
FIG. 10B is a flow diagram illustrating the feature selection method performed by the AI system shown in FIG. 1 in accordance with a representative embodiment.

FIG. 10A is a flow diagram illustrating the method of AI-based classification performed by the AI system 100 to predict retinopathies and the associated stages of progression in accordance with a representative embodiment. FIG. 10B is a flow diagram illustrating the feature selection method performed by the AI system 100 in accordance with a representative embodiment. With reference to FIG. 10A, the method of classification comprises three primary processes. The first process, represented by block 190, is OCTA image data acquisition and feature extraction (DA&FE). In accordance with a representative embodiment, an acquired OCTA dataset 191 is divided into a training dataset 192 (e.g., 80%) and a testing dataset 193 (e.g., 20%). For both the training dataset 192 and the testing dataset 193, the different OCTA features are extracted at the feature extraction block 194 in the manner described earlier.

The next of the three primary processes, which is represented by block 195, is optimal feature identification (OFI). The compiled extracted features from the training dataset 192 are used to train the SVM classifier model 150, as indicated by block 196. Training the model 150 involves performing the aforementioned hierarchical backward elimination algorithm represented by block 197 for each specific classification task to generate the combinations of features that will subsequently be used to predict retinopathies and stages of progression. The hierarchical backward elimination algorithm identifies the most sensitive feature set for each classification task. Block 198 represents configuring the model 150 during training to apply the various combinations of features selected by the backward elimination algorithm to be used for each classification task. Block 198 also represents the model 150 being used during testing to process acquired OCTA data to predict retinopathies and the corresponding stages of development.

After feature selection or optimization have been performed by the process represented by block 195, the process moves to the third primary process represented by block 201. This process uses the trained model 150 to perform multiple-task classification (MTC) on acquired OCTA data to predict whether retinal features contained in acquired OCTA data is indicative of one or more retinopathies and the corresponding stages of progression. Preferably, the classification and prediction is first tested using the cross-validated training data. Then the previously stored training data and corresponding compiled feature set is used for testing and validating the performance of the classifier model 150. Preferably, each acquired OCTA image is classified in a hierarchical manner with the first classification task identifying control (normal) subjects 202 and disease subjects 203, the second task identifying the specific disease, which is DR 204 and SCR 205 in this example, and the third task identifying the stage of the specific disease as indicated by blocks 206-208 for DR and blocks 209 and 211 for SCR. In accordance with a preferred embodiment, the backward elimination algorithm represented by block 197 is utilized simultaneously with the MTC process 201 to identify the most sensitive retinal features and to retrain the model 150 with new combinations of retinal features to be used to test patients. Block 212 represents the process of retraining the model 150.

Data Acquisition and Feature Extraction for this Study

OCTA data acquisition: In the present study disclosed herein, all patients underwent complete anterior and dilated posterior segment examination (JIL, RVPC). For DR, a retrospective study of consecutive type II diabetes patients was conducted who underwent OCT/OCTA imaging. The patients are representative of a university population of diabetic patients who require imaging for management of diabetic macular edema and DR. Two board-certified retina specialists classified the patients based on the severity of DR (mild, moderate, severe NPDR) according to the Early Treatment Diabetic Retinopathy Study (ETDRS) staging system. In case of SCR, disease stages were graded according to the Goldberg classification (stages I-V, from mild to severe). Only stages II (mild) and III (severe) SCR data were included in this study as stage I OCTA data were limited in number while stage IV OCTA images were unreliable due to distortions caused by hemorrhages and vessel proliferation. For simplification in the classification process, stages II and III were defined as mild and severe stage SCR, respectively. The control OCTA data were obtained from healthy volunteers who gave informed consent for OCT/OCTA imaging. Both eyes (OD and OS) were examined and imaged. Eyes with other ocular disease or any pathological features in their retina such as epiretinal membranes and macular edema were not included in the study. Additional exclusion criteria included eyes with prior history of vitreoretinal surgery, intravitreal injections or significant (greater than a typical blot hemorrhage) macular hemorrhages.

SD-OCT and OCTA image data were acquired using an Angiovue SD-OCT device (Optovue, Fremont, CA, USA) having a 70,000 Hz A-scan rate, and axial and lateral resolutions of ~5 μm and ~15 μm, respectively. All OCTA images used in this study were 6 mm×6 mm scans. It will be understood, however, that the inventive principles and concepts are not limited with respect to the data acquisition system that is used to acquire the OCTA images. The AI system 100 shown in FIG. 1 can be implemented in a number of ways with different types of data acquisition systems. The machine learning program 140 will train the AI classifier model 150 using OCTA training data acquired by the data acquisition system 160 being used, which can vary depending on where the system 100 is installed.

For the present study disclosed herein, OCTA images were acquired from both superficial and deep capillary plexuses (SCP and DCP). All of the OCTA images were qualitatively examined, except for OCTA images with severe motion or shadow artifacts. The OCTA images were exported from the imaging device and custom-developed MATLAB procedures were used for image processing, feature extraction and classification as described below in more detail.

OCTA pre-processing and feature extraction: All the OCTA images used in the present study had a field of view (FOV) of 6 mm×6 mm (304×304 pixels). The OCTA images were normalized to a standard window level based on the maximum and minimum intensity values to account for light and contrast image variation. Bias field correction and contrast adjustment of the OCTA images improved the overall reliability of the extracted features and concurrently the performance of the classifier model 150 to identify OCTA images from different cohorts.

Figure 11B:
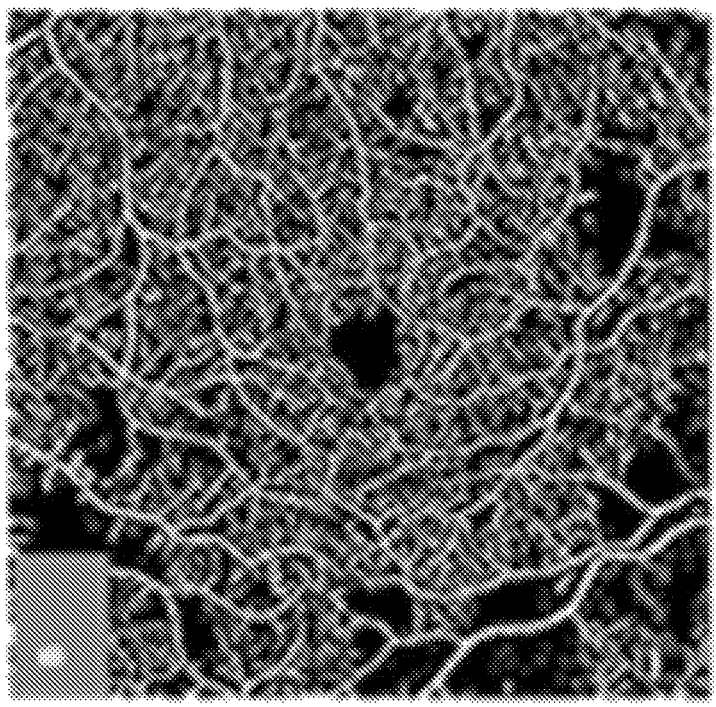
FIGS. 11A-11E are six representative OCTA images that are used herein to demonstrate an embodiment of the feature extraction process performed by the machine learning algorithm of the AI system shown in FIG. 1.
Figure 11A:
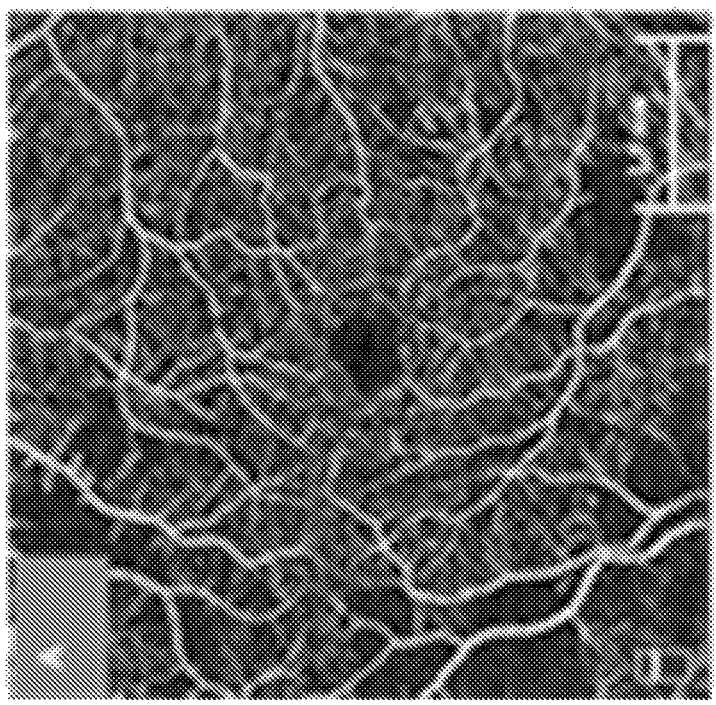
Figures 11C, 11D, 11E:
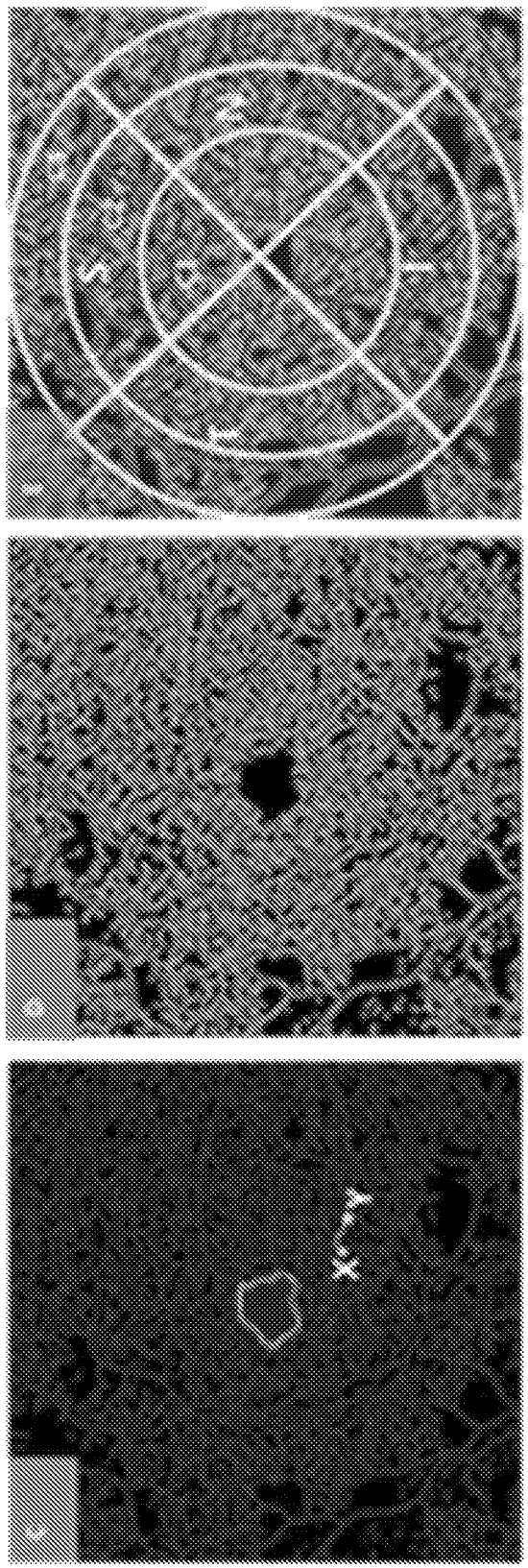

FIGS. 11A-11E are six representative OCTA images that will be used herein to demonstrate the feature extraction process. Six different quantitative OCTA features were extracted from each OCTA image for the AI classification. FIG. 11A shows the original OCTA image from a severe NPDR patient. FIG. 11B shows a segmented OCTA blood vessel map including large blood vessels and small capillaries. A Hessian-based, multi-scale Frangi vesselness filter and FD classification were used to provide a robust and accurate blood vessel map. FIG. 11C is an OCTA blood vessel skeleton map with segmented fovea (marked region) and FAZ contour. A random vessel branch is highlighted with X and Y endpoints identified. FIG. 11D is an OCTA vessel perimeter map. FIG. 11E is an OCTA fractal contour maps for blood vessel density measurement. The scale bar shown in FIG. 11A applies to all of the images shown in FIGS. 11A-11E.

The vascular features were BVT, BVC, VPI, and BVD, while the foveal features were FAZ-A and FAZ-CI. Before measuring the vascular features, the vessel map and skeleton map were extracted from the OCTA image (FIGS. 11B and 11C). The Hessian-based, multi-scale Frangi vesselness filter that was used to enhance the vascular flow information in the blood vessel map utilized the Eigen vectors of the Hessian matrices to calculate the likelihood that an OCTA region is a vascular structure. Adaptive thresholding along with morphological functions were used for cleaning the vessel map and removing noise. From the vessel map, a skeleton map was generated using morphological shrinking functions. The extracted vessel and skeleton maps from the OCTA images had an average area of 47.34% and 25.81%, respectively.

The following is a description of an example of the retinal feature measurement process performed by the AI system 100 and described above with reference to FIG. 10A. It should be understood that many variations can be made to the retinal feature measurement process described herein and that retinal features other than those discussed herein may be used for training and testing.

BVT: The BVT was measured in the SCP. For BVT measurement, the BVT of each vessel branch is measured from the skeleton map and the average BVT is measured as, $$BVT = \frac{1}{n}\sum_{i=1}^{n}\left(\frac{\text{Geodesic distance of a vessel branch } i}{\text{Euclidean distance of a vessel branch } i}\right) \quad (1)$$

$$\text{Euclidean distance} = \sqrt{(x_1 - x_2)^2 + (y_1 - y_2)^2} \quad (2)$$

$$\text{Geodesic distance} = \int_{t_0}^{t_1} \sqrt{\left(\frac{dx(t)}{dt}\right)^2 + \left(\frac{dy(t)}{dt}\right)^2} \, dt \quad (3)$$

where [xi, yi] are the two endpoints of a vessel branch.

BVC: BVC was measured from the SCP as the ratio of vascular area (calculated from vessel map) and vascular length (calculated from skeleton map), $$BVC = \frac{\text{Vascular area}}{\text{Vascular length}} \qquad (4)$$

VPI: VPI was measured from the perimeter map (FIG. 11D) in SCP as the ratio of vessel perimeter area and total image area, $$VPI = \frac{\text{Perimeter area}}{\text{Total image area}} \qquad (5)$$

BVD: BVD was measured in both SCP and DCP using fractal dimension (FD) technique. The details and rationale about FD calculation is previously described. Each pixel is assigned an FD value from 0 to 1 where 0 corresponds to avascular region and 1 corresponds to large vessel pixels. The FD of 0.7 to 1 corresponds to vessel pixels and average BVD is measured as the vascular area to total image area.

$$BVD = \frac{\text{Vascular area}}{\text{Total image area}} \qquad (6)$$

BVD the measurements were taken in three localized regions in the retina, three circular regions of diameter 2 mm, 4 mm and 6 mm (C1, C2, and C3) around the fovea (as shown in FIG. 11E). The segmented FAZ area was excluded when measuring BVD for improved diagnostic accuracy.

FAZ-A: The FAZ-A was measure in both SCP and DCP. The fovea was demarcated automatically (blue area in FIG. 11C) and FAZ-A was measured as, $$FAZ\text{-}A(\mu^2) = \text{Number of pixels is Fovea} \times \text{Area of single pixel} \qquad (7)$$

The automatically segmented FAZ area was compared to manually traced FAZ labelling and had 98.26% similarity with manually segmented ground truths.

FAZ-CI: FAZ-CI was measured in both SCP and DCP. From the demarcated fovea, FAZ contour was segmented automatically (green demarcated contour in FIG. 5C). From the segmented contour the FAZ-CI was measured as, $$FAZ - CI = \frac{\text{Perimeter of the } FAZ \text{ contour}}{\text{Perimeter of a circle with equivalant area to the } FAZ} \qquad (8)$$

Optimal Feature Identification

Statistics and classification model: Statistical analyses were conducted using MATLAB (Mathworks, Natick, MA, USA) and OriginPro (OriginLab Corporation, MA, USA). All of the OCTA features were tested for normality using a Shapiro-Wilk test. For normally distributed variables, one versus one comparisons were conducted using Student's t-test and one way, multi-label analysis of variance (ANOVA) was used to compare differences among multiple groups. If the features were not normally distributed, independent sample t-test (Mann-Whitney) were used for one versus one comparisons and non-parametric Kruskal-Wallis test for comparing multiple groups. The Chi-square test was used to compare the sex and hypertension distribution among different groups. For age distribution, ANOVA was used. Spearman's correlation coefficients ($r_s$) were measured to analyze the relationship among the OCTA features and their correlation with DR or SCR severity. Statistical significance for univariate analysis and correlation test was defined with $P<0.05$; however, the P values were Bonferroni-corrected for multiple simultaneous group comparisons.

With reference to FIG. 10B, for the backward elimination algorithm, the initial critical value of P was set to 0.15 for the univariate model (block 221) while it was set to 0.1 for multivariate model (block 223). In this case, it was determined that a P value of 0.05 or less was too conservative and could possibly result in a loss of valuable information from multivariate regression analysis of different features.

Optimal feature selection with backward elimination: For choosing the preferred, or optimal, feature combination for each classification task, the aforementioned backward elimination algorithm was used. The flowchart of FIG. 10B represents the backward elimination algorithm, which starts with all of the predictors in the model 150. A univariate model is fit with each feature and the critical P value is set as 0.15, as indicated by block 221. In an exemplary embodiment used in the present study, the features with a P value greater than 0.15 are removed in the first step and the remaining features are applied to a multivariate model, as indicated by block 223. In an iterative process represented by blocks 224-229, the variable that is least significant, i.e., the one with the largest P value with worst prediction performance in a multivariate regression analysis, is removed and the model is refitted (block 226). Each subsequent iteration removes the least significant variable in the model until all remaining variables have individual P values smaller than the critical P value (set at 0.05), as indicated by block 231. At this step, the feature set is fed to the original SVM classifier model 150.

After the classifier model 150 is trained with the optimal feature combination, the classifier model 150 will typically be tested with a testing data set. The feature selection process using backward elimination preferably is repeated for each of the steps and the classifier model 150 is trained with corresponding optimal feature combination at each step for a specific classification task. For control vs. disease and DR. vs. SCR classification, the SVM performs a binary (one vs. one) classification while for staging disease conditions (mild vs. moderate vs. severe NPDR and mild vs. severe SCR) the classifier model 150 performs multi-class classification. The prediction preferably is performed on the testing database with multi-fold (e.g., five-fold) cross validation to control any overfitting. Once the classifier model 150 is trained with the selected, and preferably optimal, feature combination, any new data can be directly inputted into the classifier model to generate task-specific predictions.

Figure 12:
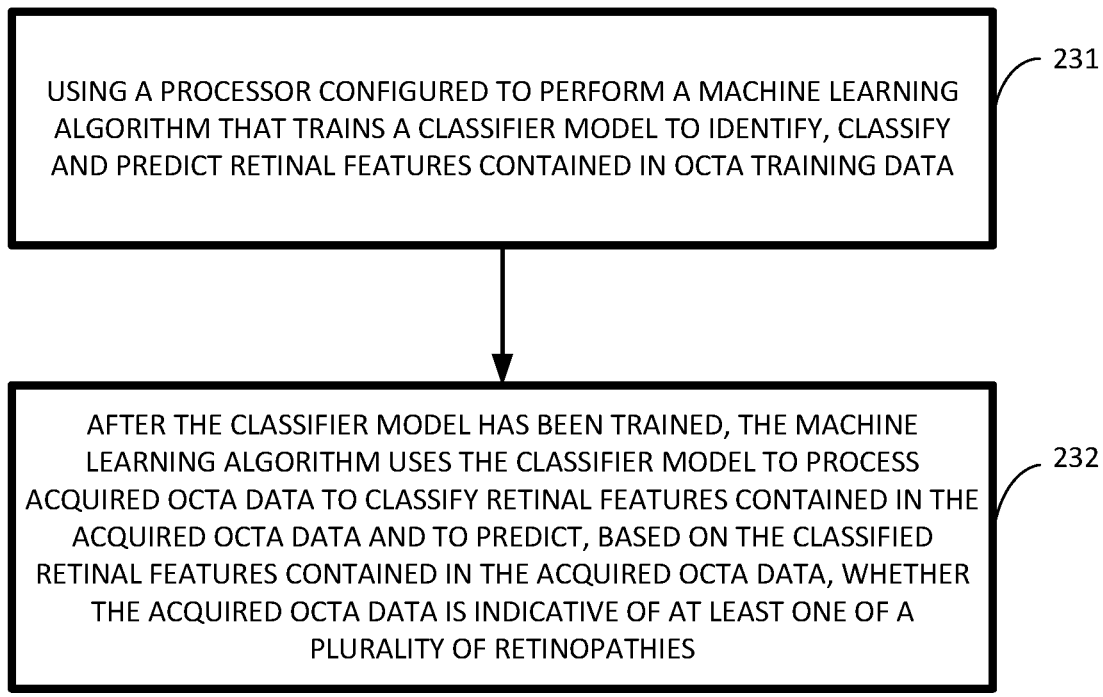
FIG. 12 is a flow diagram that represents the process performed by the processor of the AI system shown in FIG. 1 in accordance with a representative embodiment to classify retinal features and predict, based on the classified retinal features, one or more retinopathies.

FIG. 12 is a flow diagram that represents the process performed by the processor 110 of the AI system 100 shown in FIG. 1 in accordance with a representative embodiment to classify retinal features and predict, based on the classified retinal features, one or more retinopathies. The processor configured to perform the machine learning algorithm 140 trains the classifier model 150 that processes OCTA training data to identify, classify and predict retinal features contained in OCTA training data, as indicated by block 231. After the classifier model 150 has been trained, it is used to process acquired OCTA data acquired by the image acquisition system 160 to classify retinal features contained in the acquired OCTA data and to predict, based on the classified retinal features contained in the acquired OCTA data, whether the acquired OCTA data is indicative of at least one of a plurality of retinopathies, as indicated by block 232.

Figure 13:
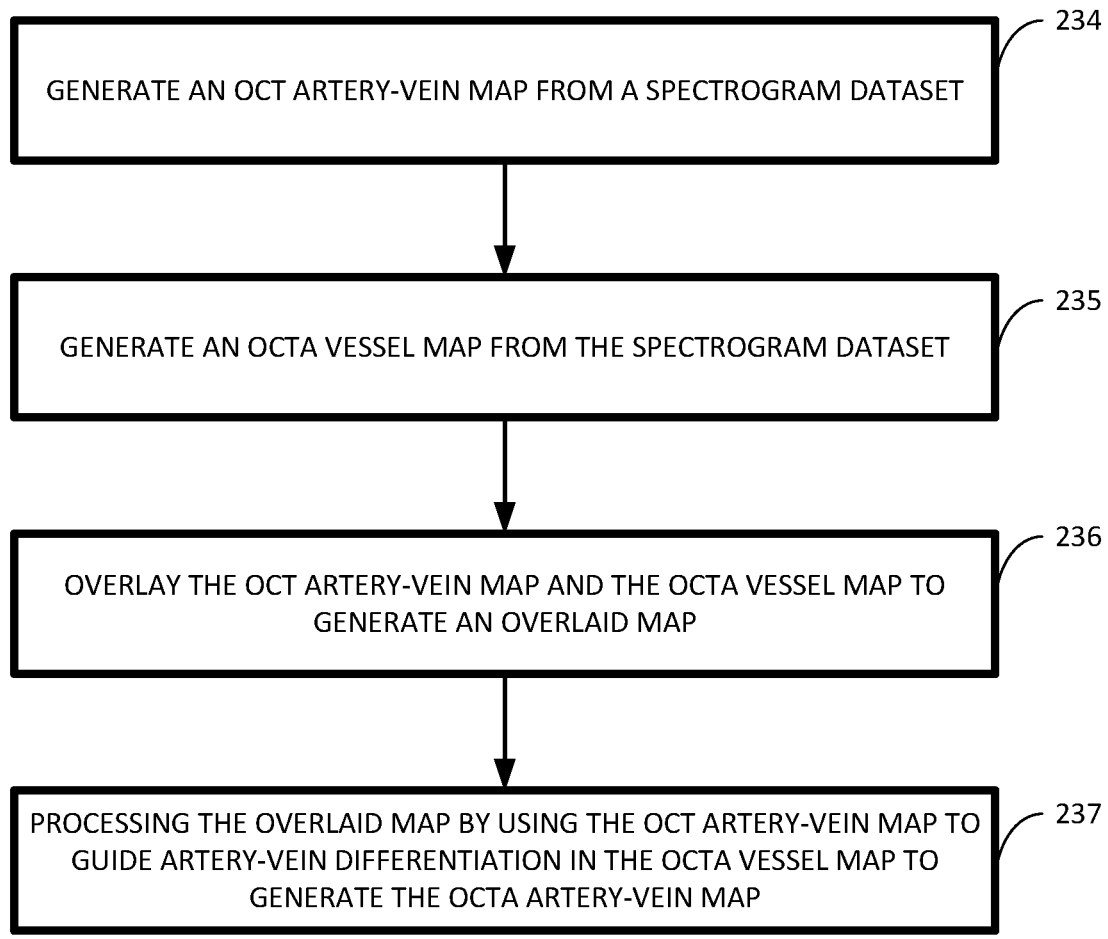
FIG. 13 is a flow diagram representing the process performed by the processor of the AI system shown in FIG. 1 to generate an OCTA artery-vein map.

In accordance with a representative embodiment, the OCTA data processed in the steps represented by blocks 231 and 232 comprises an OCTA artery-vein map. FIG. 13 is a flow diagram representing the process performed by the processor 110 shown in FIG. 1 to generate the OCTA artery-vein map. The processor 110 generates an OCT artery-vein map from a spectrogram dataset acquired by the image acquisition system 160, as indicated by block 234. The processor 110 also generates an OCTA vessel map, preferably from the same spectrogram dataset, as indicated by block 235. The processor 110 then overlays the OCT artery-vein map and the OCTA vessel map to generate an overlaid map, as indicated by block 236. The processor 110 processes the overlaid map by using the OCT artery-vein map to guide artery-vein differentiation in the OCTA vessel map to generate the OCTA artery-vein map, as indicated by block 237.

Figure 14:
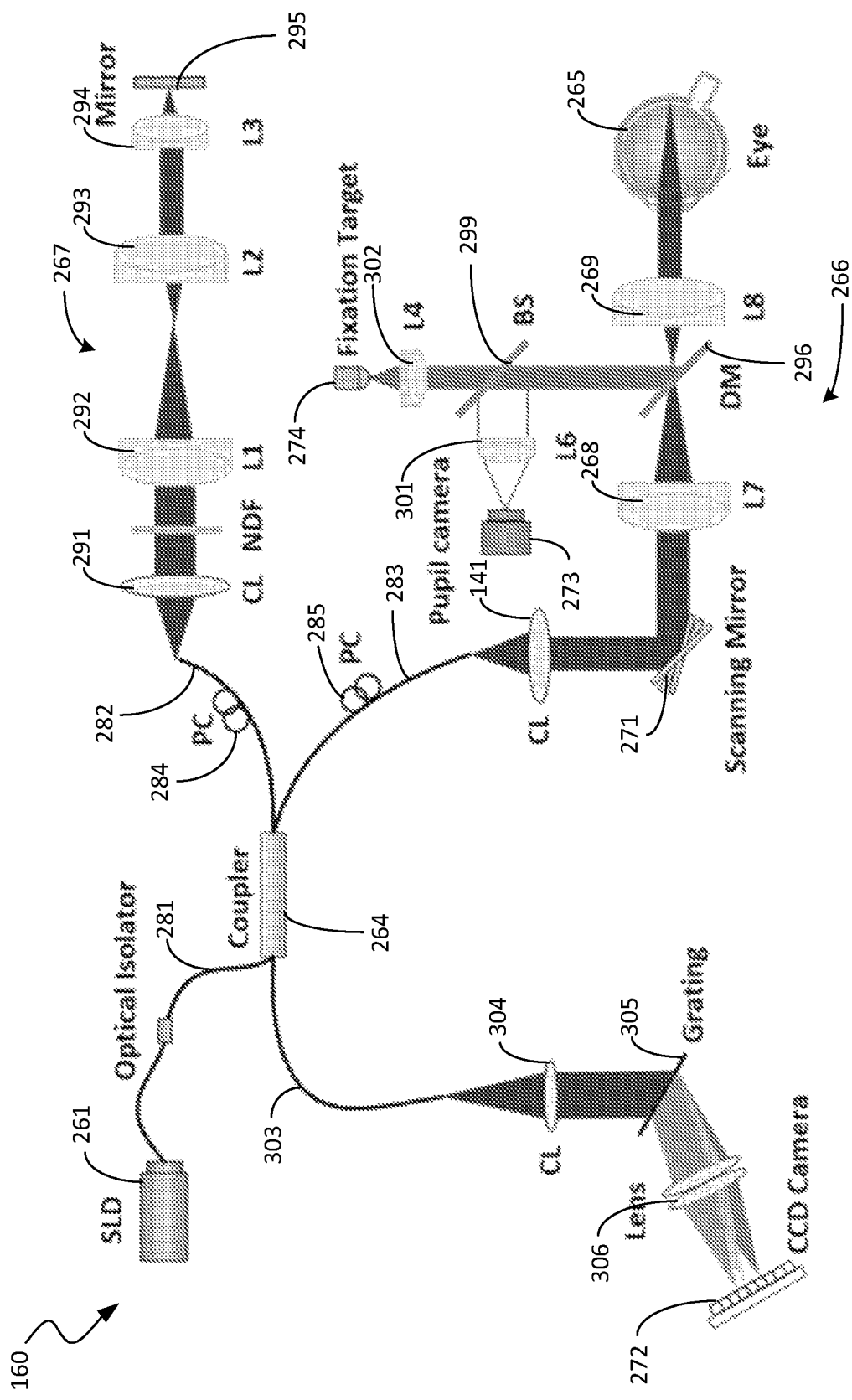
FIG. 14 illustrates a schematic diagram of a custom-designed OCT/OCTA image acquisition system that may be as the image acquisition system shown in FIG. 1 in accordance with a representative embodiment.

FIG. 14 illustrates a schematic diagram of the custom-designed OCT/OCTA image acquisition system that may be as the image acquisition system 160 shown in FIG. 1 in accordance with a representative embodiment. A light source 261 that preferably is a near infrared (NIR) superluminescent diode (SLD), having a center wavelength 810 nm (bandwidth: 760-860 nm), was selected for the present study. A fiber coupler 264 with a splitting ratio of 90:10 divides the SLD light into sample and reference light beams that travel along sample and reference arms 266 and 267, respectively, of the system 160. In the sample arm 266, the light was delivered to the eye 265 through relay optical lenses 268 and 269. One pair of scanning mirrors 271 were used to produce two-dimensional scanning over the retina of the eye 265 for OCT acquisition. A camera 272, which in the present study was a 70,000 Hz line charged coupled device (CCD) camera with 2,048 pixels, was used in the OCT spectrometer for producing the spectrogram dataset discussed above with reference to FIG. 13. The axial and lateral resolutions were estimated at 3 μm and 12 μm, respectively. A pupil camera 273 was used to aid in retinal localization, and a fixation target 274 with dim green light collimated by a lens 302 was used to minimize voluntary eye movements. For OCT recording, the illumination power on the cornea was set at ~600 μW. Four B-scan OCT images were acquired from the macular region, and speckle variance processing was used by the processor 110 (FIG. 1) as the OCTA reconstruction algorithm 130.

The image acquisition system 160 is essentially an interferometer that relies on interference between the sample light beam and the reference light beam to create an interference pattern that is captured by the CCD camera 272. Because the manner in which interferometers are used in OCT systems to produce two- and three-dimensional images of a sample is well known, a detailed discussion of the nature of the interferometer and the manner in which it operates is not provided herein in the interest of brevity. A first light beam emitted by the light source 261 that travels along a first length of optical fiber 281 to the fiber coupler 264. The fiber coupler 264 includes a beam splitter (not shown) that splits the first light beam into a reference light beam and a sample light beam that are coupled onto second and third lengths of optical fiber 282 and 283, respectively, that include respective polarization controllers (PCs) 284 and 285, respectively.

The arm 267 of the interferometer that includes the second length of fiber 282 and the PC 284 is the reference arm. The arm 266 of the interferometer that includes the third length of fiber 283 and the PC 285 is the sample arm. The reference arm 267 includes a lens system comprising lenses 291-294 and a mirror 295. The lens system 291-294 can have a variety of configurations of various types of optical elements. In accordance with this representative embodiment, the lens system includes first, second, third and fourth lenses 291, 292, 294 and 294, respectively. As shown in FIG. 14, these lenses perform various collimating and focusing functions on the reference light beam passing out of the end of the second length of optical fiber 282 and reflected from the mirror 295.

The arm 266 of the interferometer that includes the third length of fiber 283 and the PC 285 is the sample arm. The sample arm 266 includes a lens system 268 and 269, the pair of scanning mirrors 271 and a dichroic mirror 296. The lens system 268, 269 of the sample arm 266 can have a variety of configurations of various types of optical elements. A portion of the light reflected from the eye 265 is reflected by the mirror 296 onto mirror 299. The light reflected by the mirror 299 is coupled by a lens 301 the pupil camera 273.

The reference and sample light beams reflected by the mirror 295 and by the sample 265, respectively, are combined in the optical coupler 264 and the combined signal is coupled into an end of a fourth length of optical fiber 303. The combined signal passing out of the opposite end of the fourth length of optical fiber 303 is collimated by a collimating lens 304 and the collimated light beam is directed onto a diffraction grating 305 that performs wavelength division demultiplexing to separate the light into different wavelengths of light. The different wavelengths of light are directed by lenses 306 onto different areas of a sensor array of the CCD camera 272. The diffraction grating 305, the lenses 306 and the sensor array of the camera 272 form a spectrometer. The scanning mirrors 271 have the effect of producing three-dimensional images on the sensor array.

One eye of each volunteer was used for OCT recording. During the alignment for retinal imaging, the subject was instructed to follow the fixation target 274, while the operator monitored the real-time OCT scans and pupil camera 273 to locate a region-of-interest (ROI). Once the desired ROI was identified, the subject was asked to keep his eyes wide open and refrain from blinking during the image acquisition. The acquired spectrogram dataset is then processed by the processor 110 in the manner described above with reference to FIG. 13 to generate the OCTA artery-vein map that may be used by the process described above with reference to FIG. 12.

It should be noted the inventive principles and concepts described above with reference to FIGS. 13 and 14 may be used independently of the inventive principles and concepts described above with reference to FIGS. 1-12. The OCTA artery-vein map obtained at the step represented by block 237 in FIG. 13 is useful in diagnosing multiple eye diseases. Early clinical diagnosis and prompt medical intervention are essential for preventing vision loss due to eye diseases. It is known that many eye diseases can target arteries and veins differently. For example, venous loops, venous beading and arterial narrowing have been reported in DR and SCR patients. Therefore, differential artery-vein analyses can lead to better sensitivity for disease detection and staging classification. The artery-vein ratio of blood vessel caliber, for example, has been reported as a predictor of eye conditions. Manual differentiation of retinal artery-vein is time consuming, and it can only be performed by experienced ophthalmologists. Therefore, a number of algorithms have been proposed to explore automated artery-vein differentiation in fundus photography. However, a fundus image has limited resolution and sensitivity to reveal microvascular abnormalities associated with eye conditions. Often, microvascular anomalies that occur early on in these ocular diseases cannot be reliably identified in traditional fundus photography.

By providing depth-resolved capability for visualizing multiple retinal layers with capillary level resolution, quantitative OCT and OCTA contribute to better clinical management of eye diseases. Multiple OCTA features have been developed for quantitative OCTA analysis and objective classification of DR, AMD, glaucoma, and SCR. Nonetheless, differential artery-vein analysis is not available for existing clinical OCTA instruments.

Recently, the feasibility of using color fundus image to guide artery-vein differentiation in OCTA was demonstrated. Two differential artery-vein features, i.e., artery vein ratio of blood vessel caliber (AVR-BVC) and tortuosity (AVR-BVT), improved the performance of OCTA detection and classification of DR. However, clinical deployment of this method is quite difficult due to the requirements of two clinical instruments, i.e., a fundus camera and OCTA system, and sophisticated image registration.

In accordance with inventive principles and concepts described above with reference to FIGS. 13 and 14, intensity-based feature analysis in OCT can be employed to guide a unique artery-vein differentiation in OCTA. In principle, an en face OCT image functions as a near infrared fundus image, and thus retains reflectance intensity-based features in the vascular profiles. The central reflex is larger in arteries, whereas the vessel caliber is larger in veins. The brightness profiles and optical density in arteries are brighter compared to neighboring veins. In other words, the overlaid map is used to perform OCT-guided artery-vein classification in OCTA.

In accordance with a representative embodiment, the OCT artery-vein map and the OCTA vessel map are generated from the same raw spectrogram captured by the camera 272. The OCT artery-vein map and the OCTA vessel map are overlaid to generate the overlaid map, which may be displayed on the display device 170 (FIG. 1). The overlaid map is then used to guide artery-vein differentiation in the OCTA vessel map to generate the OCTA artery-vein map. Because the OCTA vessel map and the OCT artery-vein map can both be derived from the same spectrogram, the need to perform image registration and the need for a fundus camera and OCTA system are eliminated.

Recently, combined color fundus oximetry analysis and blood vessel tracking were combined to guide artery-vein classification in OCTA. In accordance with inventive principles and concepts described herein, the en face OCT image functions as a color fundus image to conduct optical density (OD) analysis. The OD, i.e., the light absorbance of each blood vessel, relative to surrounding tissue, can be estimated as $\ln(I_{\lambda,0}/I_\lambda)$, where $I_\lambda$ and $I_{\lambda,0}$ are the average intensity values inside and immediately adjacent area to a blood vessel with illumination light wavelength $\lambda$. It is known that the oxyhemoglobin ($HbO_2$) and deoxyhemoglobin (Hb) absorptions are sensitive to wavelength. OD ratio (ODR) between those measured at oxygen sensitive wavelengths and isosbestic wavelengths is linearly proportional to blood oxygen saturation. The ODR can be used for artery-vein classification and can be calculated as $$ODR_\lambda = \frac{OD_{sensitive}}{OD_{isosbestic}}$$

where $OD_{sensitive}$ and $D_{isosbestic}$ are optical densities at oxygen-sensitive (765 nm) and oxygen-isosbestic wavelengths (805 nm), respectively. In order to optimize the sensitivity of ODR analysis used for artery-vein classification, the 765 nm wavelength was selected as the oxygen-sensitive wavelength. The 855 nm wavelength has been used as the oxygen-sensitive wavelength for OCT oximetry analysis, with limited signal to noise ratio. The extinction coefficient difference between $HbO_2$ and Hb around 765 nm is 2.76 times higher than 855 nm used in previous studies. For comparative assessment, the ODRs was quantified for both 765 nm/805 nm and 855 nm/805 nm combinations.

Figure 27:
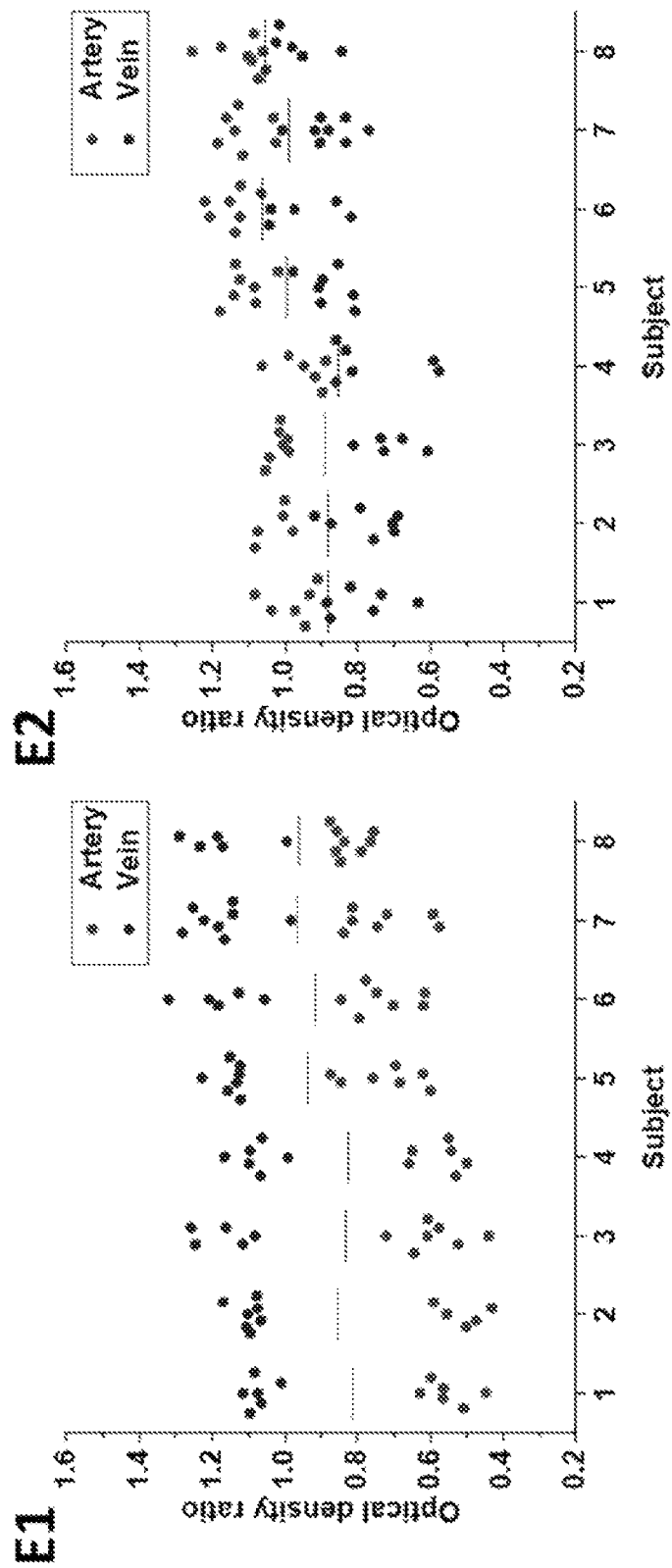
FIG. 27 shows plots E1 and E2 of ODRs from all subjects for 765/805 nm wavelength analysis (E1) and 805/855 nm wavelength analysis (E2), respectively.
Figure 28:
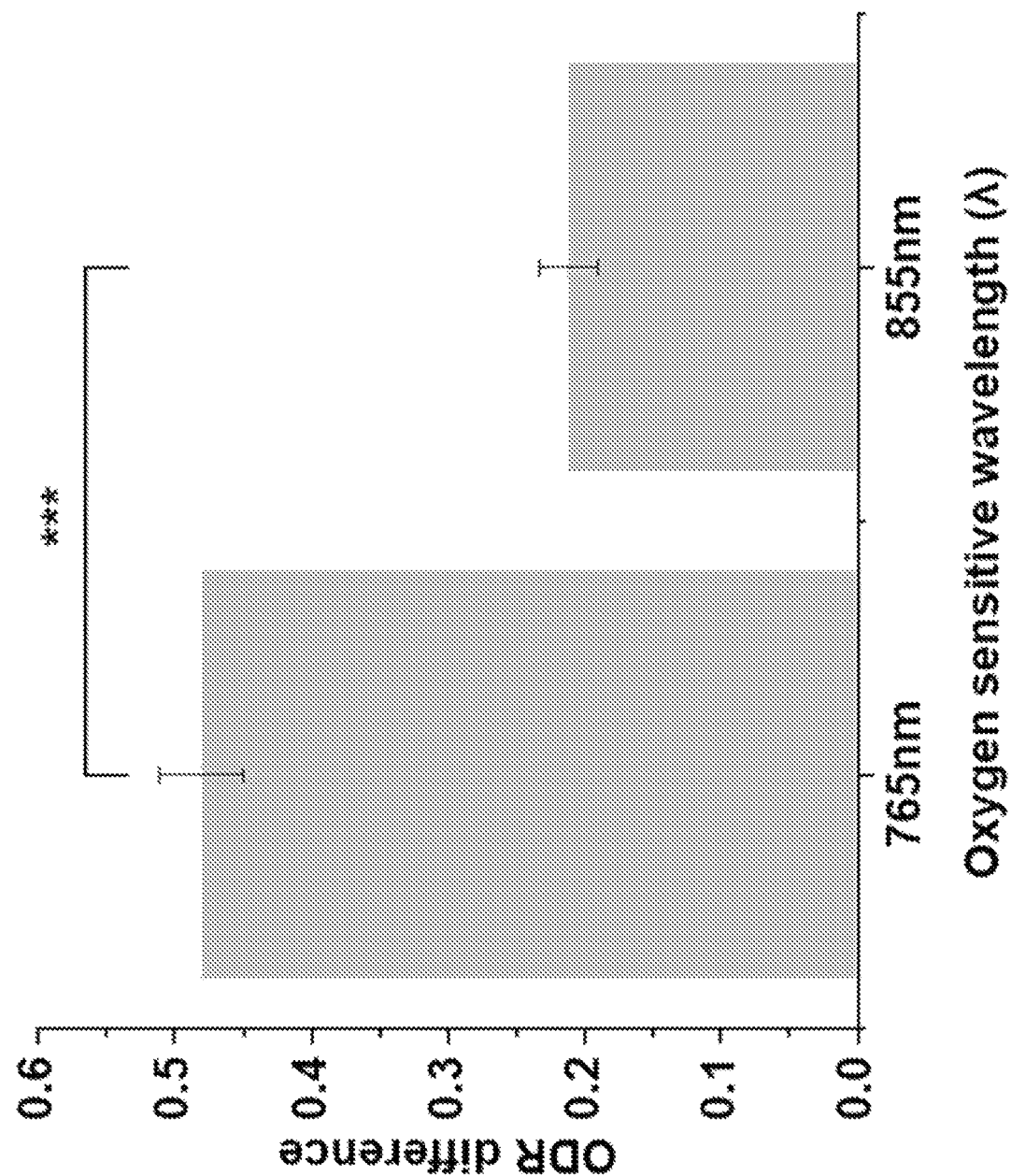
FIG. 28 is a plot the ODR difference between artery and vein as a function of ODR sensitivity.

In order to ensure reliable artery-vein classification, the ODR analysis was conducted at the optic disc region in en face OCT, and blood vessel tracing was used to track the arteries and veins into the macular region, as will be described below in more detail with reference to FIGS. 26-28. Use of the MR light source 261 in the image acquisition system 160 allowed the en face OCT image to act as a NIR fundus image in that it retains reflectance intensity-based features in the vascular profiles that allow the image to be used for artery and vein classification.

Figure 15:
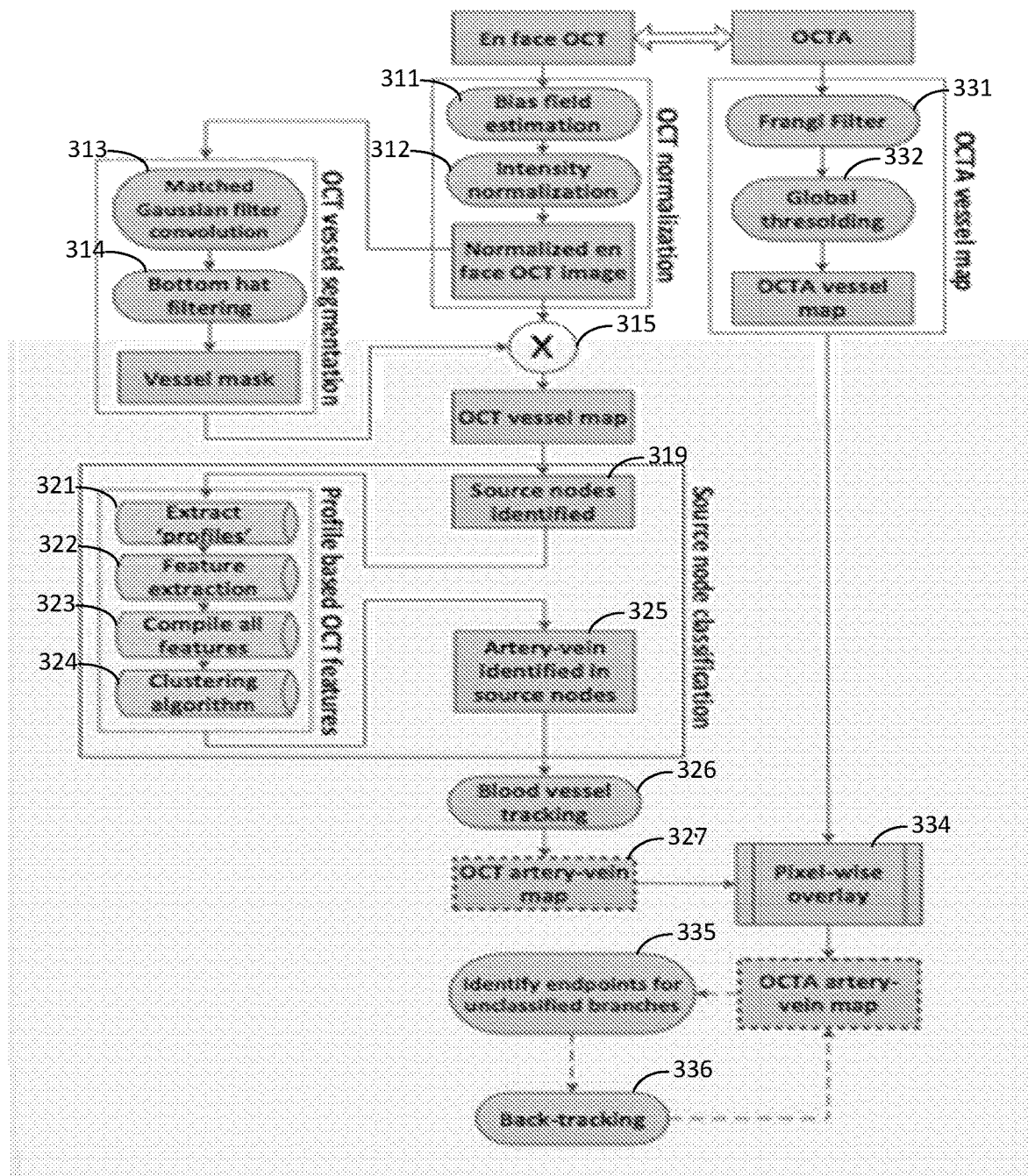
FIG. 15 is a flow diagram that illustrates method steps for performing OCT-guided artery-vein classification in OCTA in accordance with a representative embodiment.

FIG. 15 is a flow diagram that illustrates method steps for performing OCT-guided artery-vein classification in OCTA in accordance with a representative embodiment. FIGS. 16A-16E are images illustrating OCT normalization and vessel segmentation. FIG. 16A is an original en face OCT image captured by the image acquisition system 160. FIG. 16B shows a bias field estimation of the intensity inhomogeneity of the en face OCT image shown in FIG. 16A. Bock 311 in FIG. 15 represents the process of the processor 110 performing the bias field estimation. FIG. 16C shows the normalized en face OCT image corrected for intensity inhomogeneity by dividing the en face OCT image by the estimated bias field, as indicated by block 312 in FIG. 15. The en face OCT images are often affected by intensity inhomogeneity. This artifact can mislead further image analysis. Preferably the bias field correction technique is implemented to remove the intensity inhomogeneity before performing OCT feature analysis. This technique estimates the bias field that accounts for the inherent intensity inhomogeneity (FIG. 16B) and divides the image by that estimated bias to generate a normalized intensity image (FIG. 16C).

The en face OCT image can be modeled as, $$I(x,y) = b(x,y) I_{true}(x,y) \tag{9}$$

where I(x, y) is the intensity of the en face OCT image in (x, y) coordinates, $I_{true}(x, y)$ is the bias field corrected image and b(x, y) is the estimated bias field that accounts for the intensity inhomogeneity of the en face OCT image.

The bias field b(x) can be defined by, $$b(x) = \sum_{k=1}^{M} w_k \cdot G_k \tag{10}$$

where G is the set of smooth basis functions which ensures the smooth varying property of the bias field. 20 polynomials of the first three degrees are chosen as the basis functions. The bias field estimation is performed by calculating the optimal coefficients $w=[w_1, w_2, \ldots w_M]$. After the bias field b(x, y) is calculated, the intensity normalized image $I_{true}$ is obtained by dividing the en face OCT image, I, by the bias corrected field.

FIG. 16D shows an edge enhanced image generated by processing the corrected en face OCT image shown in FIG. 16C with matched Gaussian filter convolution and bottom hat filtering, as indicated by blocks 313 and 314 in FIG. 15. FIG. 16E shows a binary vessel map obtained from the image shown in FIG. 16E. FIG. 16F is a segmented en face OCT vessel map obtained by multiplying the image shown in FIG. 16C by the binary vessel map shown in FIG. 16E, as indicated by multiplier block 315 shown in FIG. 15. From the intensity normalized image shown in FIG. 16C, only the vessel information is required for following analysis. Blocks 313 and 314 in FIG. 16 represent the matched filtering combined with bottom hat filtering, respectively, to enhance and extract the blood vessel map from the corrected en face OCT image. For the match filtering, 2D Gaussian kernels of 12 different orientations and 10 different sizes were implemented to match blood vessels. These kernels cover all the blood vessel diameters and directions. They are defined as $$I(x, y) = \frac{1}{\sigma\sqrt{2\pi}} e^{-\frac{(y\cos\theta - x\sin\theta)^2}{2\sigma^2}} \quad (11)$$

where x, y are pixel coordinates; θ=rotation angle of each kernel, θ ranges from 0 to π; and σ=kernel width. The en face OCT image is convolved with 120 kernels after subtracting the mean from each kernel. In the process of cross-correlation, the features matching the kernels (representing blood vessels of various widths) produce larger coefficient values.

Larger coefficient values representing the vessel structures are selected to produce the segmented blood vessel map (FIG. 16D) from a maximum intensity projection of all the convolved images. The bottom hat filter with dimension of 20×20 pixels is then used to reduce further background variance due to uneven illumination. A global thresholding method is used to extract the binary blood vessel map (FIG. 16E). The binary map is multiplied (multiplier 315) with the intensity-normalized en face OCT image to generate the segmented vessel map of the en face OCT image (FIG. 16F). This en face OCT vessel map is used for further source node identification and artery-vein tracking.

Figures 17A, 17B, 17C:
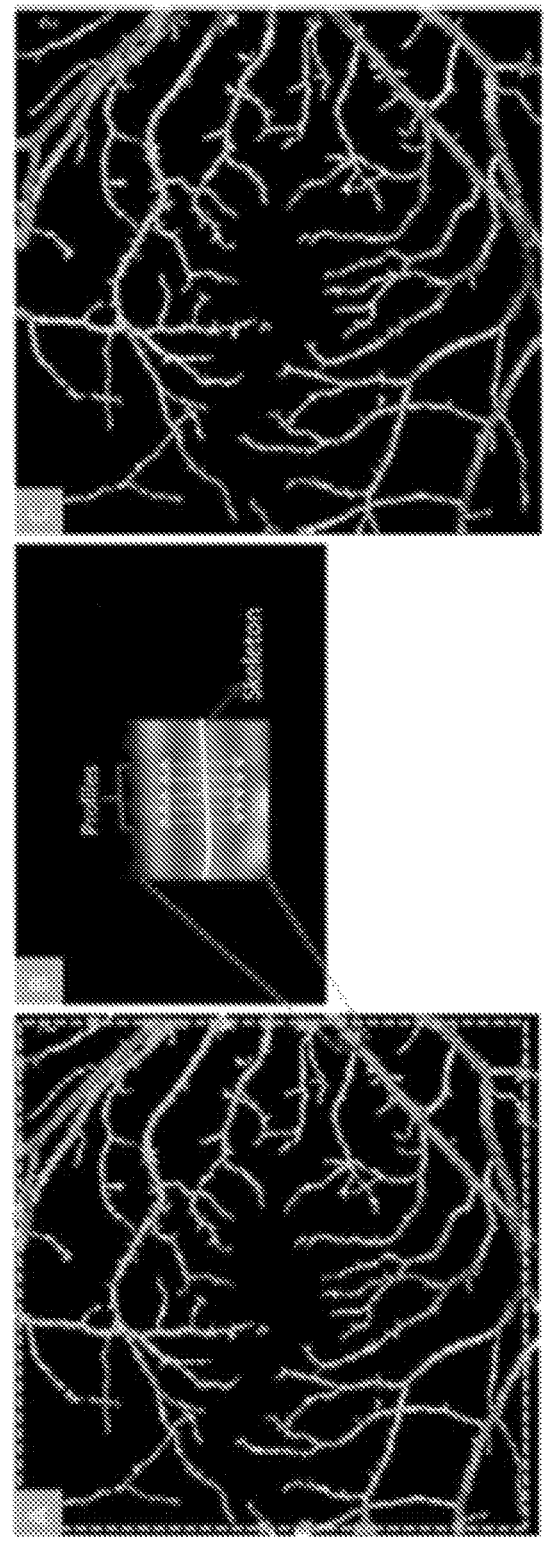
FIG. 17A shows a segmented en face OCT vessel map with source nodes in the map identified with yellow crosses in the step represented by block 319 in FIG. 15.
FIG. 17B is an enlargement of a sample source node segment (marked with red circle in A) of the vessel map shown in FIG. 17A.
FIG. 17C shows the en face OCT vessel map with each of the identified source nodes identified as artery (red) or vein (blue).

FIG. 17A shows the segmented en face OCT vessel map with source nodes in the map identified with yellow crosses by the step represented by block 319 in FIG. 15. FIG. 17B is an enlargement of a sample source node segment (marked with red circle in A) of the vessel map shown in FIG. 17A. Blocks 321-324 shown in FIG. 15 represented steps for generating profile-based OCT features that are used for source node classification. Sample profiles (marked with yellow dots in FIG. 17B) are extracted from each segment for further feature extraction and artery-vein classification. FIG. 17C shows the en face OCT vessel map with each of the identified source nodes identified as artery (red) or vein (blue).

With respect to block 319, the first step of identifying source nodes in the en face OCT vessel map is to identify source nodes at the boundary. Features are then extracted to classify them as artery or vein, as indicated by blocks 321-323. Around each of the boundaries of the vessel map, a gradient line is drawn (green dotted lines in FIG. 17A). These gradient lines can identify blood pixels from the background based on intensity information. The identified source node points are marked with yellow crosses in FIG. 17A. After the vessel source nodes along the boundary of the vessel map are selected, multi-feature analysis is employed on the vessel source nodes to classify them into artery and veins (red/blue nodes at the boundary of FIG. 17C). The features are extracted from the source node segments and are based on the concept of 'profile'. From each of the source node segments, multiple profiles perpendicular to the vessel skeleton along the vessel are extracted. The number of profiles depends on the size of the source node segments.

In the present study, the profiles are set to have a distance of two pixels among each other along the vessel skeleton. For example, if a vessel skeleton within the source node segment is 40 pixels long, the first profile will be extracted at the middle point, pixel 20. Then, the profiles will be extracted at 2-pixel intervals in both directions. In this study, the maximum number of profiles is set at 20 and minimum is 5. In case of a segment smaller than 5 pixels in length, profiles are taken from all of the pixels. From each source node segments (S), N numbers (range, 5 to 20) of profiles are extracted. So, each segment will have a profile set 'PS$_i$' equal to S×N, where i is the number of source nodes in one image. Total profile set PS for one image is then [PS$_1$, PS$_2$, PS$_3$, . . . PS$_i$].

Figure 18:
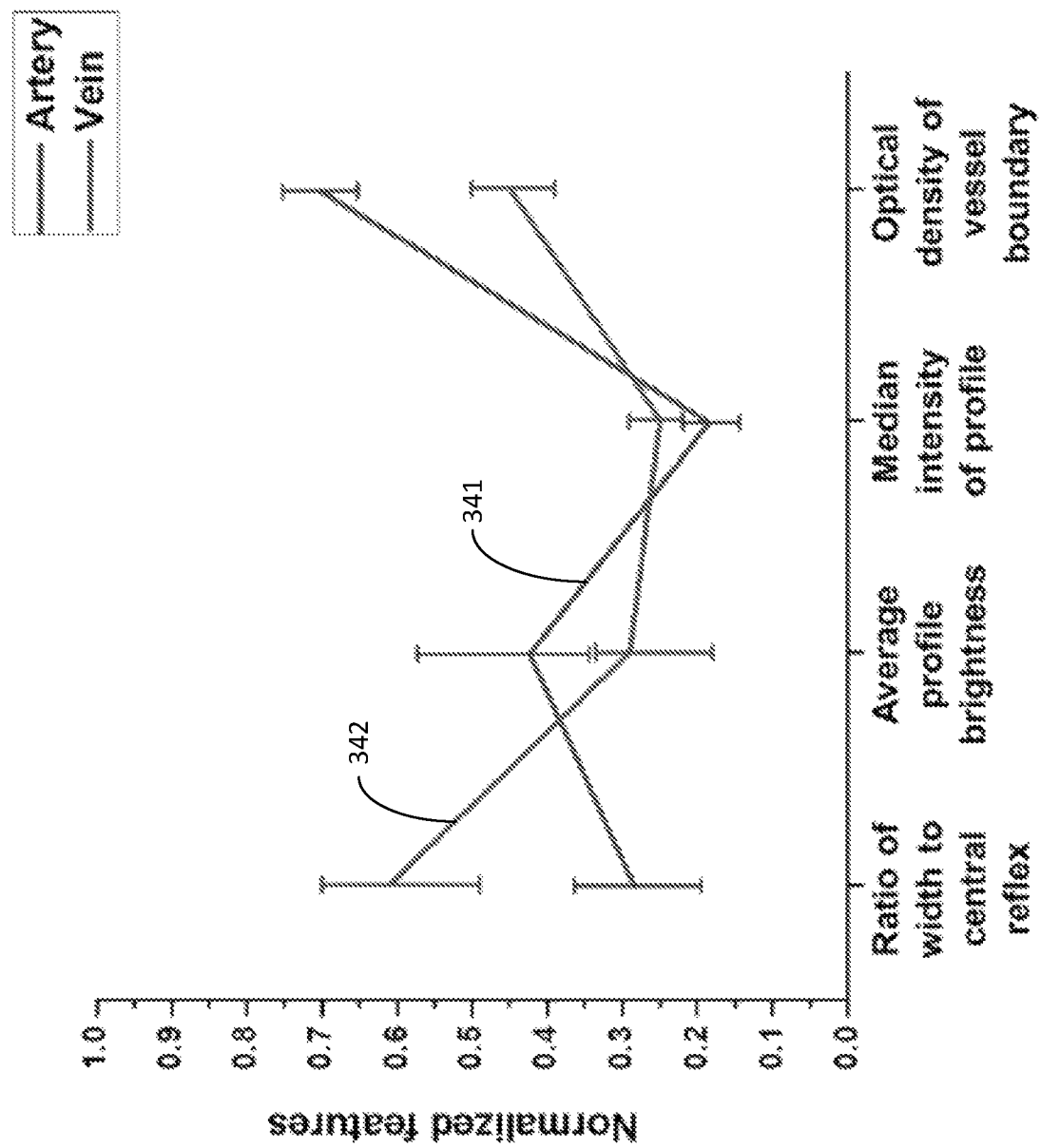
FIG. 18 shows plots of the average feature distribution in artery and vein, respectively, with the features normalized to a range of 0 to 1 for comparison in the same y axis.

For this study, four features are measured from each of the profiles: i) ratio of vessel width to central reflex, ii) average profile brightness, iii) median intensity of profile, and iv) optical density of boundary intensity compared to background intensity. FIG. 18 shows plots 341 and 342 of the average feature distribution in artery and vein, respectively, with the features normalized to a range of 0 to 1 for comparison in the same y axis.

After the feature extraction, a clustering algorithm (block 324) is used to classify source nodes as artery and vein. K-means algorithm is chosen as the clustering algorithm due to its computational simplicity and efficiency. The centroids of each class (artery and vein in our case) are set initially to the maximum and the minimum of the K-means input set, as the cluster centers of two classes should be as far as possible. The cluster centers of both the classes are calculated by the algorithm, and feature vectors are classified thereafter using the standardized Euclidian distance metric. Theoretically, the empirical probability of a certain source node to be classified as an artery ($P^{SA}$) or a vein ($P^{SV}$) is defined by, $$P^{SA} = \frac{n_A}{n_A + n_V} \text{ and } P^{SV} = \frac{n_V}{n_A + n_V} \quad (12)$$

The clustering algorithm 324 can include the following: 1) the K-means algorithm is applied to all the source node segments; 2) the image is divided into four quadrants centered at the fovea, and the K-means of each quadrant is calculated separately. Separate estimation of these four quadrants can minimize the effect of the uneven intra-image intensity distribution among the quadrants; 3) Four quadrants are rotated and the clustering algorithm is applied to each rotated quadrant. This allows overlapped areas and a vessel can be classified eight times (360 degrees, rotated each time by 45 degrees). These classification results are combined for taking the final classification decision so that the influences of different outliers are reduced. In this approach, the average classification probability P for an artery or vein source node is the mean of classification probability of all the quadrants where that vessel source node was found.

Once the source nodes are identified as artery and vein (block 325), the whole vessel map (skeleton) is tracked from the source nodes using a blood vessel tracking algorithm (block 326) that uses curvature angle information to classify the rest of the vasculature into artery or vein to produce the final OCT artery-vein map (block 327), also referred to herein as the skeleton map. FIG. 19A shows the en face OCT vessel map with the source nodes classified (block 319). FIG. 19B shows the en face OCT vessel map with the arteries and veins classified (block 327). FIG. 19C shows the original captured OCTA image.

For generating the OCTA vessel map, a Hessian based multi-scale Frangi filter (block 331) was first used on the original OCTA image shown in FIG. 19C to enhance the vascular flow information. Frangi filtering methodology uses the Eigen vectors of Hessian matrices and computes the likeliness of an OCTA region being a vascular structure. Adaptive thresholding and morphological functions (block 332) were then used for cleaning the vessel map and removing small capillary mesh structures that are not feasible for vessel tracking algorithms.

The en face OCT artery-vein map (FIG. 19B) is then overlaid with the OCTA vessel map (FIG. 19D) at the step represented by block 334 to generate an overlaid map (FIG. 19E) that is used to generate an OCTA artery-vein map (FIG. 19F). The OCTA artery-vein map. The en face OCT and OCTA images are generated from 3D projection of OCT B-scans and B-Scan speckle variance images, respectively. This means the structural coordinates of both images are same. Therefore, any process of image registration is not required for the overlaying process. This means that artery-vein classification information of en face OCT ($X_{OCT}$, $Y_{OCT}$) are transferred to corresponding OCTA ($X_{OCTA}$, $Y_{OCTA}$) coordinates. The OCTA vessel map has some additional vascular structures compared to the en face OCT map. For each of the additional branches, the endpoints and corresponding branch points are identified in the skeleton using morphological functions and the endpoints are then back-tracked and linked to the already identified artery-vein branches (blocks 335 and 336). The tracking employs textural, morphological and optical density information and includes protocols for two, three or four-way intersections, gaps in the tracking path and overlapping of artery or vein. The final OCTA artery-vein map is shown in FIG. 19F.

To test and validate the system and methods described above with reference to FIGS. 13-19F, this study used a sample of 100 OCT/OCTA images captured from 50 subjects. All OCT and OCTA images were acquired using an SD-OCT angiography system (Angiovue, Optovue, Fremont, CA, USA), with a 70-kHz A-scan rate, and axial and lateral resolutions of ~5 μm and ~15 μm, respectively. Among the 50 subjects, 20 had DR, 20 had SCR patients and 10 were control subjects. For every subject, images were acquired from both eyes (OD and OS). All DR and SCR patients underwent a complete anterior and dilated posterior segment examination (JIL). Control data were obtained from healthy volunteers. Subjects with prior intravitreal injections, vitreous surgery or history of other eye diseases were not included. Eyes with significant ocular pathology, (epiretinal membranes, vein occlusion or macular edema) were also excluded. OCT or OCTA images with severe motion artifacts were excluded.

All analyzed en face OCT and OCTA images were 8 mm×8 mm scans (Angiovue SD-OCT system, Revue software version 2018.0.0.14; the scan pattern was raster with 304 A-lines and 304 frames). The en face OCT images included all retinal layers and excluded the choroidal layer. OCTA images from the superficial layer, which generally includes 80% of ganglion cell complex (GCC), containing all structures of inner plexiform layer (IPL) up to the border with inner nuclear layer (INL), were used. The segmentation of the superficial layer was conducted with the commercially available software of Angiovue SD-OCT system (ReVue). The en face OCT and OCTA data were exported from the ReVue, and further image analysis, feature extraction and artery-vein classification tasks were conducted in custom-developed MATLAB (Mathworks, Natick, MA, USA) procedures with graphical user interface (GUI).

Figures 20A, 20B:
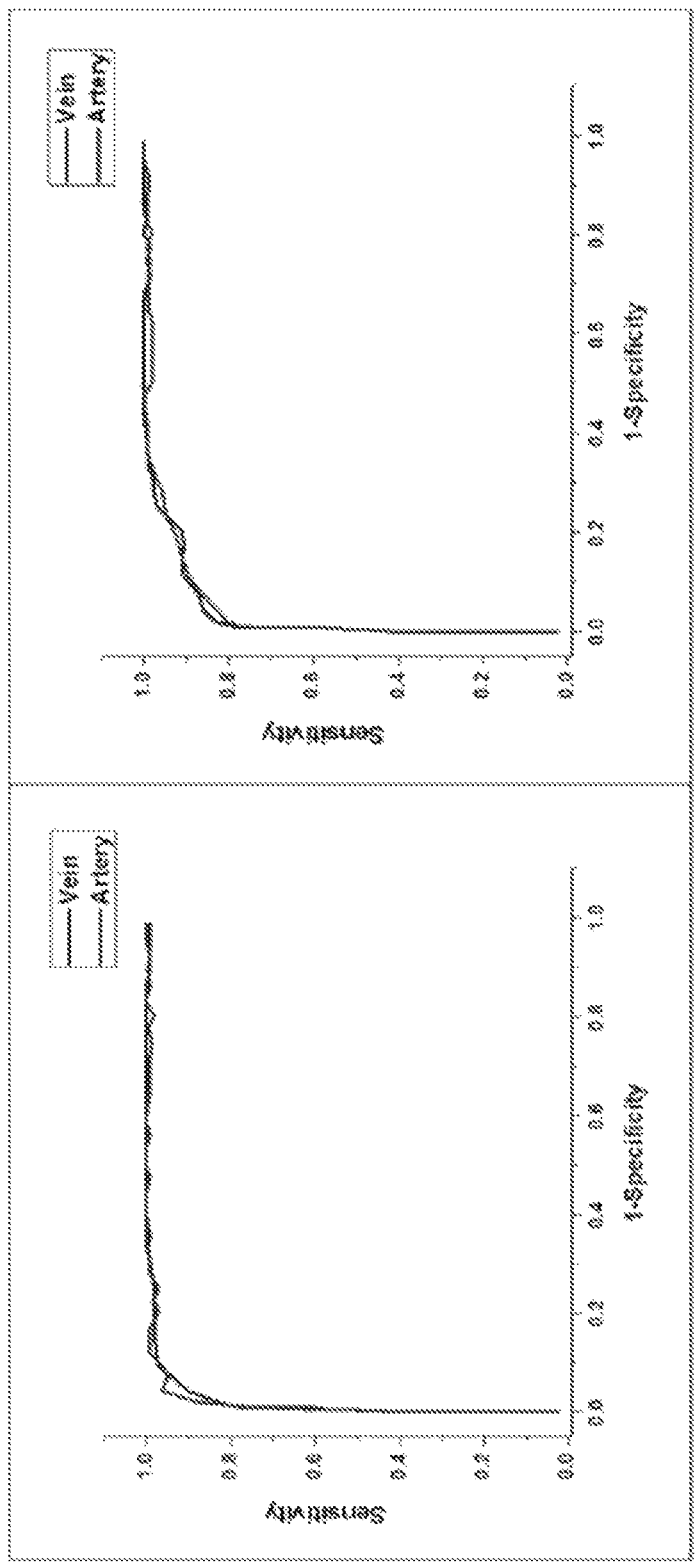
FIGS. 20A and 20B are plots of vein and artery mean ROC curves for en face OCT and OCTA images, respectively.

For evaluating the classification performance, sensitivity, specificity and accuracy metrics were calculated. An ROC curve and corresponding area under the ROC curve (AUC) was also measured. ROC curve plots the 'sensitivity' (true positive rate) as a function of '1-specificity' (false positive rate) at different cutoff points. The closer the ROC curve is to the upper left corner, the more accurate the prediction is. AUC measures how well the classifier is able to identify the two classes (artery and vein). A 100% AUC represents a perfect prediction whereas lower than 50% represents bad prediction. Separate evaluation metrics for artery and vein are measured with respect to the labeled ground truths. FIGS. 20A and 20B are plots of vein and artery mean ROC curves for en face OCT and OCTA images, respectively.

The performances of artery-vein classification in OCT and OCTA are summarized in Table 7 and Table 8, respectively, shown in FIGS. 21 and 22, respectively. These artery-vein classification results with the automated feature analysis are validated with the ground truth vessel maps manually labeled by two experienced observers (JIL and DT). The ground truths only refer to vessel map areas with identical artery and vein assignments by these two independent graders. The two observers had 97.01% and 94.56% agreements respectively on the marked artery-vein vessel maps for en face OCT and OCTA images. Manual labelling is performed on the binary vessel maps in both cases. The observers manually traced the binary vessel maps with red (artery) and blue (vein) markings and identified each branchpoint with yellow markings.

All of the manually labelled source nodes, branchpoints and artery-vein branches are matched pixel by pixel with the classified artery-vein map to generate the performance metrics. Specific areas in the vessel map for which the two observers do not agree on are identified as unclassified.

The results demonstrate 96.89% and 96.59% accuracies in identifying artery and vein source nodes, respectively, in the en face OCT images (ICC 0.98 and 0.97 for 2-repeat measurement, 95% confidence interval (CI) 0.93-1). There are 97.16% sensitivity and 95.73% specificity for artery identification; 96.64% sensitivity and 96.15% specificity for vein identification. For the entire en face OCT vessel map, 96.81% and 96.33% accuracies were observed in identifying artery and vein source nodes, respectively, in the en face OCT images (ICC 0.96 and 0.97 for 2-repeat measurement, 95% confidence interval (CI) 0.91-0.97).

There are 97.07% sensitivity and 95.29% specificity for artery identification; 96.52% sensitivity and 96.14% specificity for vein identification. In the case of classifying OCTA images, average accuracy is 96.51% for all vessels; 97.08% sensitivity and 94.98% specificity for artery identification; 96.30% sensitivity and 95.01% specificity for vein identification are observed. The accuracies are 96.77% and 96.25%, respectively, for identifying a blood vessel as artery and vein in the OCTA images (ICC 0.94 and 0.91 for 2-repeat measurement, 95% CI 0.87-0.96). The performance metrics were averaged for all OCTA images. The artery-vein classification accuracy for OCTA images from DR, SCR and control cohorts were 96.82%, 94.37% and 98.34%, respectively.

Figure 23:
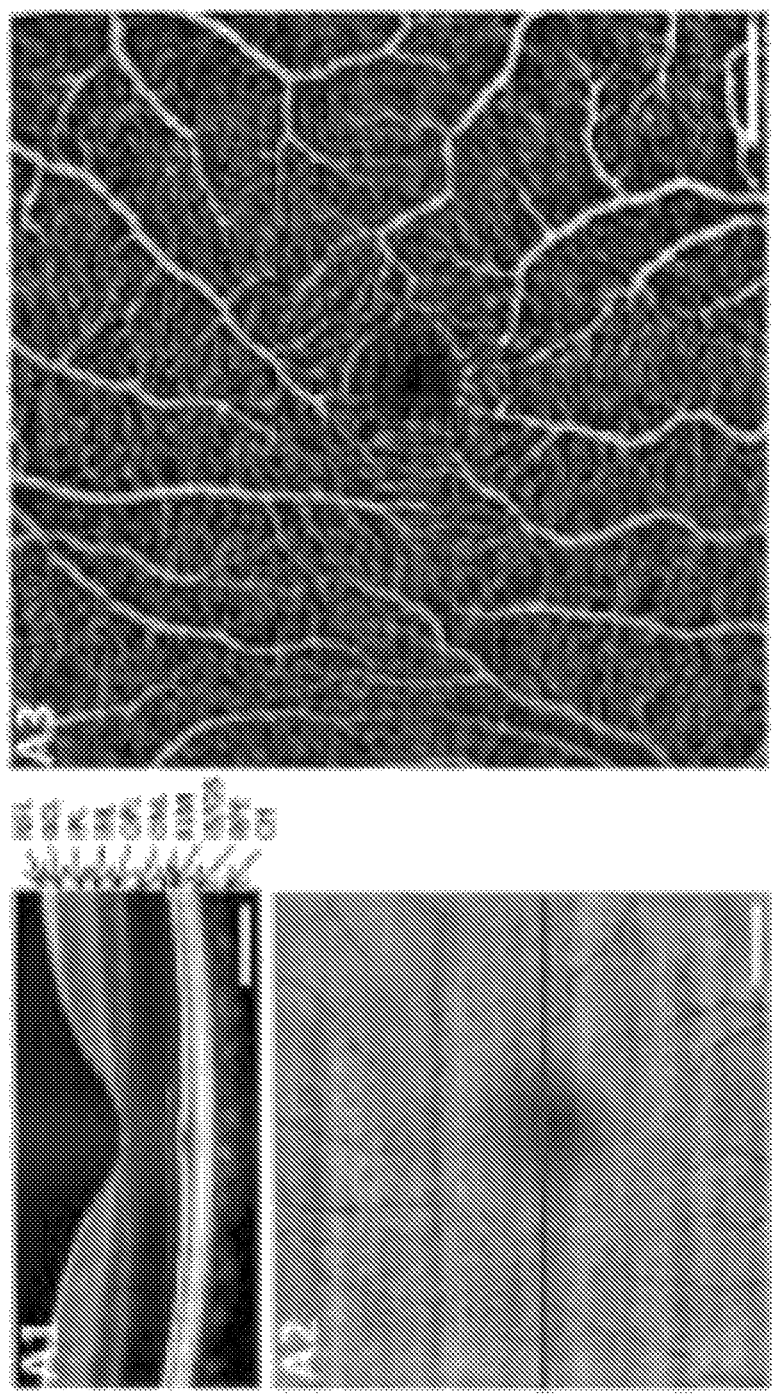
FIG. 23 shows a representative B-scan OCT image (A1), an en face OCT image (A2) and an OCTA image (A3) of the macular region.

FIG. 23 shows a representative B-scan OCT image (A1), an en face OCT image (A2) and an OCTA image (A3) of the macular region. The B-scan OCT image (A1) clearly revealed individual layers in the retina, including the nerve fiber layer (NFL), the ganglion cell layer (GCL), the inner plexiform layer (IPL), the inner nuclear layer (INL), the outer plexiform layer (OPL), the outer nuclear layer (ONL), the external limiting membrane (ELM) layer, the inner segment/outer segment (IS/OS), the retinal pigment epithelium (RPE) and the choroid (CH) (A1). The en face OCT image (A2) enabled fundus visualization of the macula (fovea), and retinal blood vessels (7A2). In comparison with the en face OCT image (A2), the OCTA image increased the visibility of blood vessels with capillary level resolution (A3). The en face OCT and OCTA images consist of 350×350 pixels, corresponding to a 3.5 mm×3.5 mm retinal area.

Figure 24:
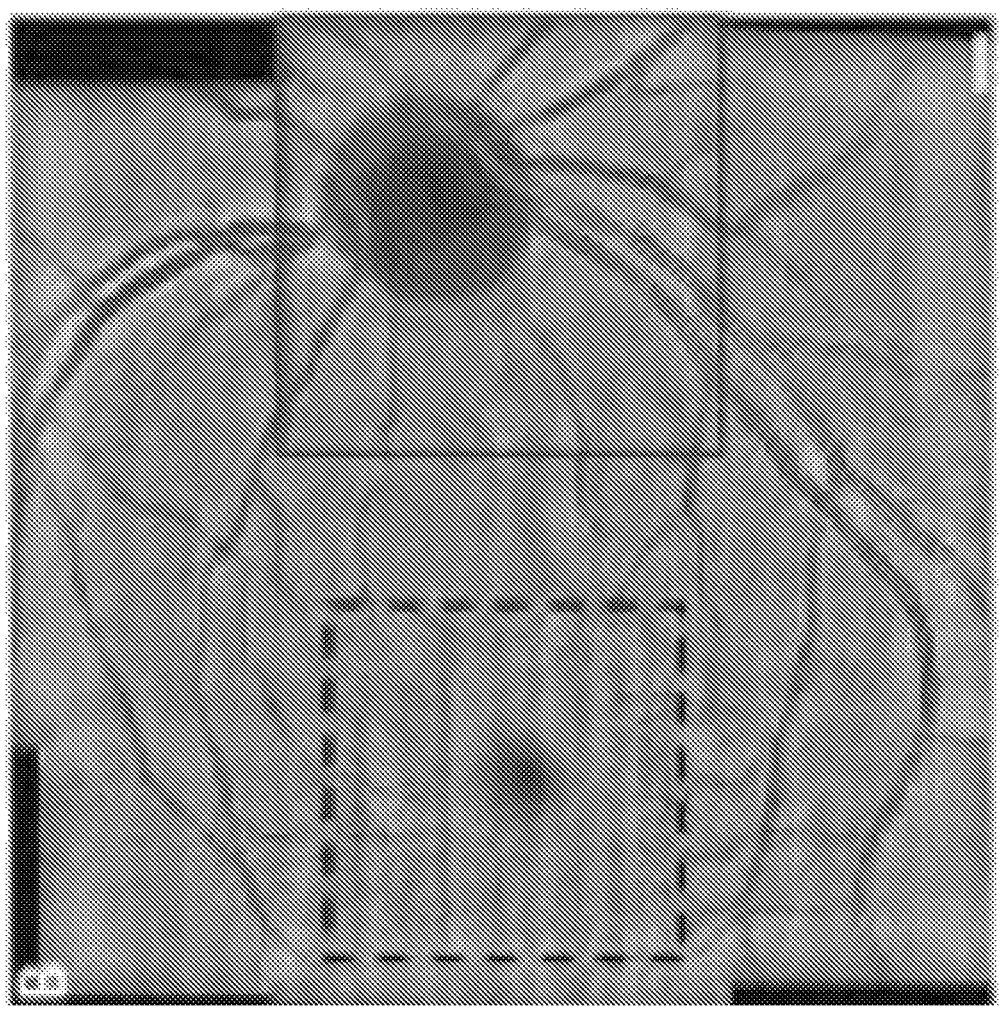
FIG. 24 shows a retinal OCT fundus image that covers both the optic disc and macular regions to overcome difficulties associated with artery-vein classification of small blood vessels around the macular region.

Direct artery-vein classification of small blood vessels around the macular region is difficult due to the small dimension and limited contrast compared to background intensity (A2). FIG. 24 shows a retinal OCT fundus image that covers both the optic disc and macular regions to overcome difficulties associated with artery-vein classification of small blood vessels around the macular region. Nine OCT volumes were collected to produce the OCT fundus image shown in FIG. 24.

Figure 25:
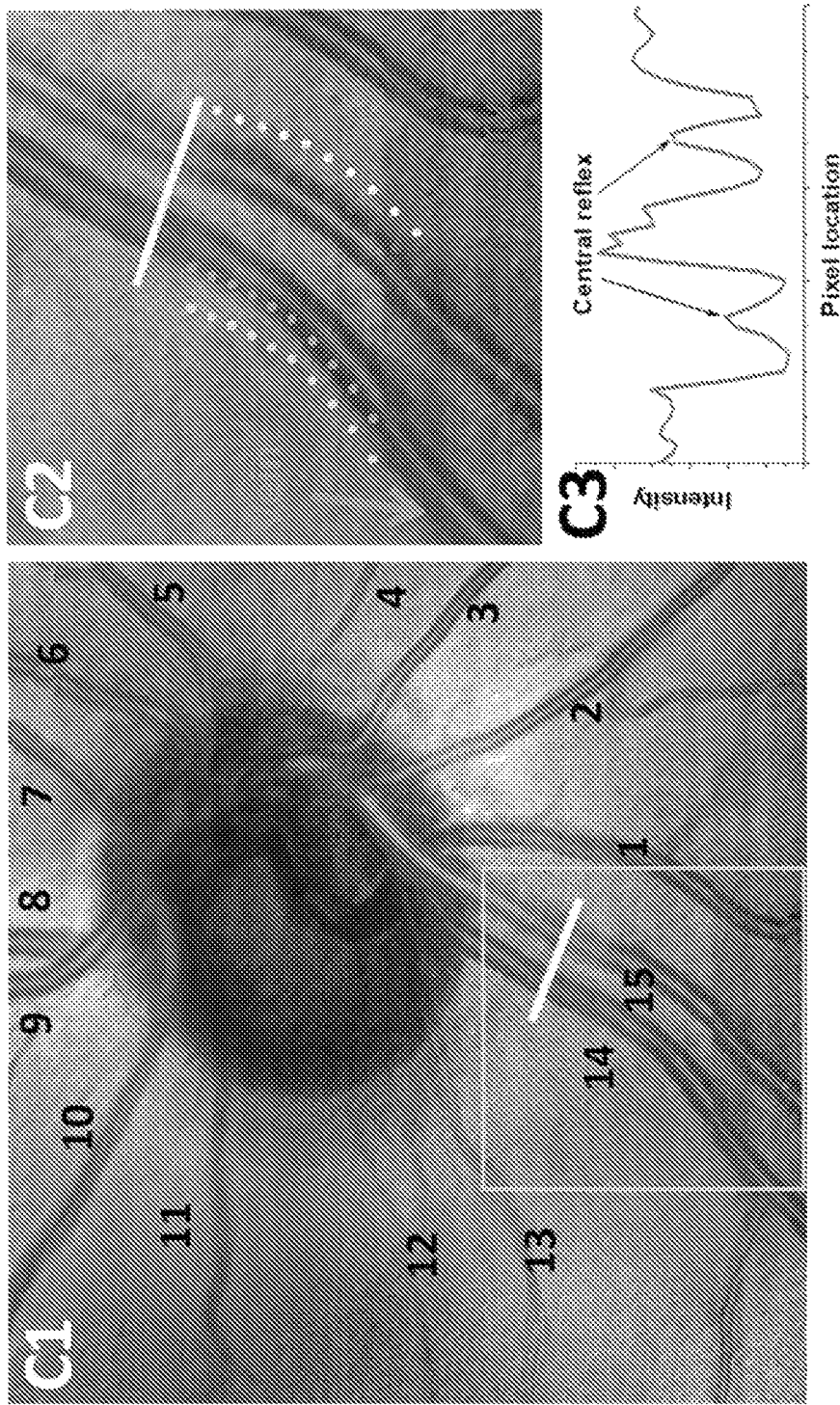
FIG. 25 shows the blood vessels within the optic disc region having relatively large diameter, and thus that are capable of being used for artery-vein classification.

FIG. 25 shows the blood vessels within the optic disc region (C1). These blood vessels have relatively large diameter, and thus can be readily used for artery-vein classification. Ten sampling locations were selected from the edge and surrounding tissue for normalized ODR analysis (C2). The edges of the blood vessels were chosen to reduce the influence of central reflex (C3).

Figure 26:
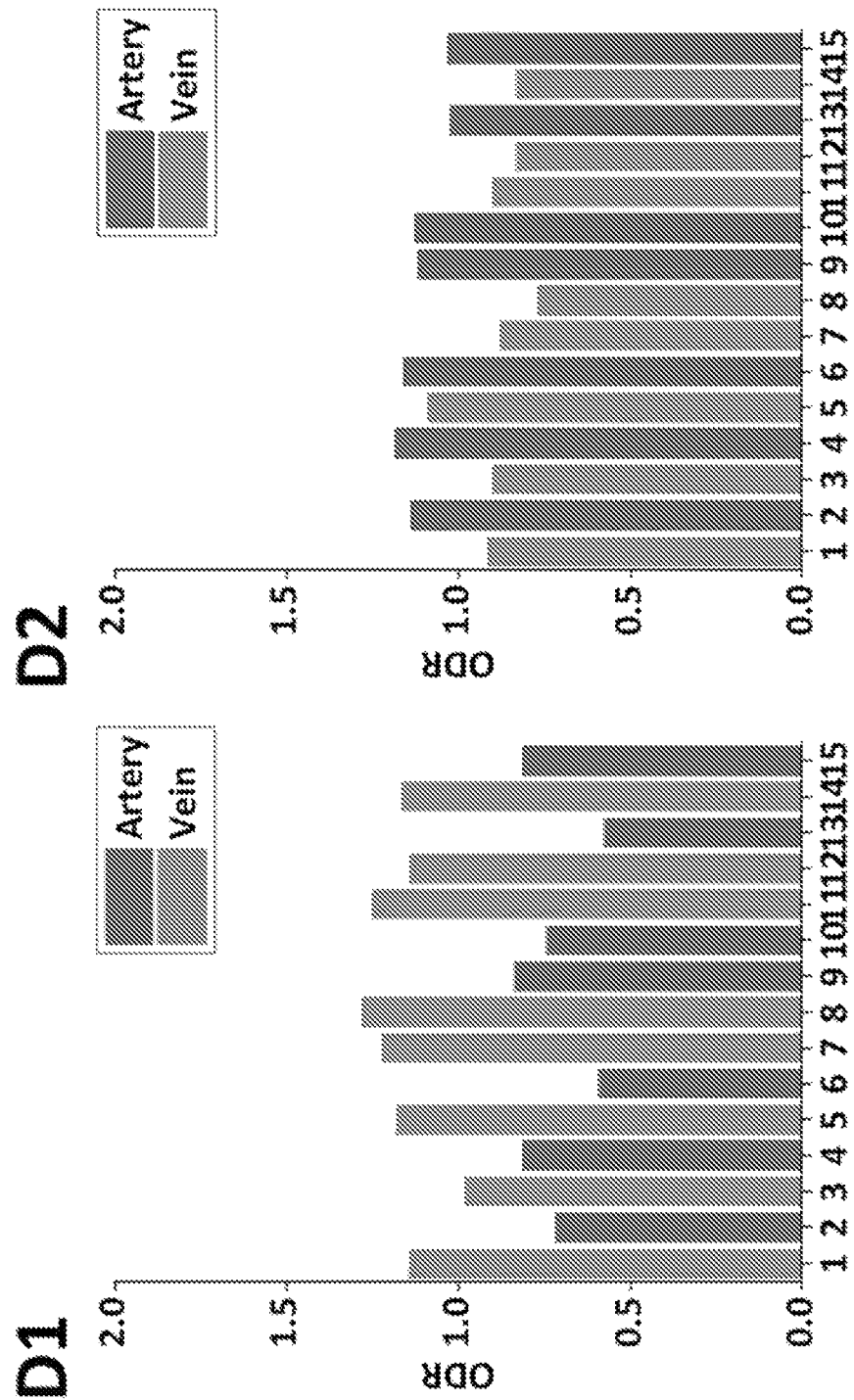
FIG. 26 shows plots D1 and D2 of optical density ratios (ODRs) of individual blood vessels shown in FIG. 25 using 765 nm and 855 nm, respectively, as oxygen-sensitive wavelengths, respectively.

FIG. 26 shows plots D1 and D2 of optical density ratios (ODRs) of individual blood vessels in FIG. 25, C1 using 765 nm and 855 nm, respectively, as oxygen-sensitive wavelengths, respectively. Arteries consistently revealed smaller ODRs compared to that of the veins at 765 nm wavelength (FIG. 26, D1) and larger ODRs in arteries compared to that of the veins at 855 nm wavelength (FIG. 26, D2). FIG. 27 shows plots E1 and E2 of ODRs from all subjects. The averaged ODR of all vessel nodes can work as a practical thresholding criterion to separate arteries and veins readily for 765/805 nm analysis (E1), while the averaged ODR cannot be used to reliably separate arties and veins for 805/855 nm analysis (E2). FIG. 28 is a plot the ODR difference between artery and vein as a function of ODR sensitivity. The ODR difference showed 2.29 times higher at 765 nm oxygen-sensitive wavelength (0.48±0.03; mean±standard error) than 855 nm oxygen-sensitive wavelength (0.21±0.02; mean±standard error).

Figure 29:
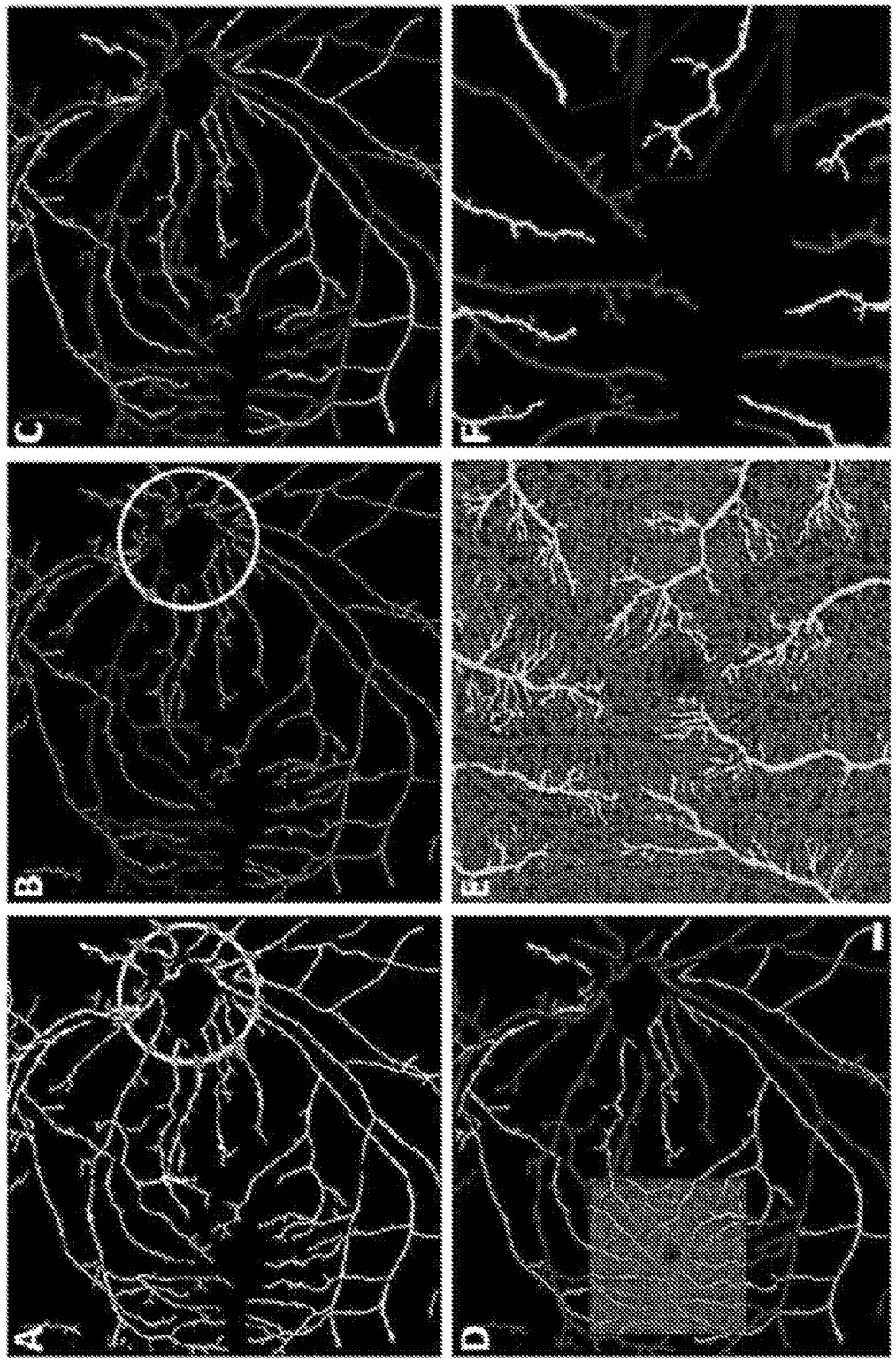
FIG. 29 shows images demonstrating the manner in which the OCT artery-vein map can be used to guide the artery-vein classification in the OCTA image.

FIG. 29 shows images demonstrating the manner in which the OCT artery-vein map can be used to guide the artery-vein classification in the OCTA image. Upon a segmented vessel map corresponding to the en face OCT image in FIG. 24 obtained by implementing the global thresholding method 332 (FIG. 15), and the optic disc is identified based on gradient intensity information. The source nodes are detected around the optic disc to make a start point for each vessel tracking and identified as red and blue for artery and vein, respectively, based on the above ODR analysis. A skeletonized vessel map for the vessel tracking is shown in FIG. 29 in image B. The blood vessel tracking algorithm started at a nodal point and tracked the branch until it reached the end point within macular region. The procedure was completed until all branches were classified into arteries or veins. FIG. 29, image C shows the OCT artery-vein map generated by inverse distance transform.

Because the OCTA image was reconstructed based on speckle variance analysis of the OCT, the OCTA image is naturally registered with the OCT image (FIG. 29, image D). Therefore, the OCT artery-vein map (FIG. 29, image C) can be used to guide the artery-vein classification in the OCTA image (FIG. 29, image D). Upon registration, the OCT artery-vein map was mapped into the OCTA image. The blood vessel branches in the OCTA image were connected with the branches in OCT artery-vein map. They were further tracked from branches of OCT artery-vein map to the end of OCTA branches accordingly. The tracking algorithm and artery-vein classification followed the same protocol used for creating the OCT artery-vein map. FIG. 29, image E shows the OCTA artery-vein map guided by OCT artery-vein map. The arteries and veins in the macular region were fully classified, showing more capillary details compared to the OCT artery-vein map of the same macular region (FIG. 29, image F).

In summary, the feasibility of using OCT intensity profile feature analysis to guide artery-vein differentiation in OCTA is set forth herein. In comparison with ground truths prepared by experienced ophthalmologists, this automated method has been able to differentiate individual arteries and veins in clinical OCTA with 96.51% accuracy.

It should be noted that any or all portions of algorithms described above that are implemented in software and/or firmware being executed by a processor (e.g., processor 110) can be stored in a non-transitory memory device, such as the memory 110. For any component discussed herein that is implemented in the form of software, any one of a number of programming languages may be employed such as, for example, C, C++, C #, Objective C, Java®, JavaScript®, Perl, PHP, Visual Basic®, Python®, Ruby, Flash®, or other programming languages. The term "executable" means a program file that is in a form that can ultimately be run by the processor 110. Examples of executable programs may be, for example, a compiled program that can be translated into machine code in a format that can be loaded into a random access portion of the memory 120 and run by the processor 110, source code that may be expressed in proper format such as object code that is capable of being loaded into a random access portion of the memory 120 and executed by the processor 110, or source code that may be interpreted by another executable program to generate instructions in a random access portion of the memory 110 to be executed by the processor 110, etc. An executable program may be stored in any portion or component of the memory 120 including, for example, random access memory (RAM), read-only memory (ROM), hard drive, solid-state drive, USB flash drive, memory card, optical disc such as compact disc (CD) or digital versatile disc (DVD), floppy disk, magnetic tape, static random access memory (SRAM), dynamic random access memory (DRAM), magnetic random access memory (MRAM), a programmable read-only memory (PROM), an erasable programmable read-only memory (EPROM), an electrically erasable programmable read-only memory (EEPROM), or other like memory device.

It should be noted that the inventive principles and concepts have been described with reference to representative embodiments, but that the inventive principles and concepts are not limited to the representative embodiments described herein. Although the inventive principles and concepts have been illustrated and described in detail in the drawings and in the foregoing description, such illustration and description are to be considered illustrative or exemplary and not restrictive; the invention is not limited to the disclosed embodiments. Other variations to the disclosed embodiments can be understood and effected by those skilled in the art, from a study of the drawings, the disclosure, and the appended claims.

What is claimed is:

1. An artificial intelligence (AI) system that classifies retinal features and predicts, based on the classified retinal features, one or more retinopathies, the AI system comprising:
a processor configured to perform a machine learning algorithm, the machine learning algorithm performing a process comprising:
training a classifier model to identify, classify and predict retinal features contained in optical coherence tomography angiography (OCTA) training data, where the classifier model utilizes a hierarchical backward elimination technique to identify a plurality of combinations of retinal features used in the training process to train the classifier model to identify and classify retinal features contained in the acquired OCTA data; and
after the classifier model has been trained, using the classifier model to process acquired OCTA data acquired by an image acquisition system to classify retinal features contained in the acquired OCTA data based at least in part upon the plurality of combinations of retinal features and to predict, based on the classified retinal features contained in the acquired OCTA data, whether the acquired OCTA data is indicative of at least one of a plurality of retinopathies; and
a memory device in communication with the processor, the memory device storing the classifier model, OCTA training data and acquired OCTA data.

2. The AI system of claim 1, wherein when the processor performing the machine learning algorithm uses the classifier model to predict, based on the classified retinal features contained in the acquired OCTA data, whether the acquired OCTA data is indicative of at least one of a plurality of retinopathies, the processor also predicts a respective stage of development of said one or more retinopathies ranging from non-proliferative stages to proliferative stages of development.

3. The AI system of claim 1, wherein the process of training the classifier model comprises configuring the classifier model to identify the plurality of combinations of retinal features contained in the OCTA training data and to associate each of the plurality of combinations of retinal features with a respective retinopathy.

4. The AI system of claim 3, wherein the process of training the classifier model comprises configuring the classifier model to identify the plurality of combinations of retinal features contained in the OCTA training data and to associate one or more of the plurality of combinations of retinal features with a respective stage of development of the respective retinopathy.

5. The AI system of claim 3, wherein the process of using the classifier model comprises identifying at least one of the combinations of retinal features contained in the acquired OCTA data and predicting, based on the identification of said at least one of the combinations of retinal features contained in the acquired OCTA data, whether the acquired OCTA data is indicative of at least one of a plurality of retinopathies and a respective stage of development of the respective retinopathy.

6. The AI system of claim 5, wherein each combination of retinal features includes two or more of: blood vessel tortuosity (BVT), blood vascular caliber (BVC), vessel perimeter index (VPI), blood vessel density (BVD), foveal avascular zone (FAZ) area (FAZ-A), or FAZ contour irregularity (FAZ-CI).

7. The AI system of claim 6, wherein the process performed by the machine learning algorithm further comprises:
retraining the classifier model to identify at least one different combination of retinal features based at least in part on the prediction of whether the acquired OCTA data is indicative of at least one of a plurality of retinopathies.

8. The AI system of claim 2, wherein when the processor performing the machine learning algorithm uses the classifier model to predict, based on the classified retinal features contained in the acquired OCTA data, whether the acquired OCTA data is indicative of at least one of a plurality of retinopathies and a respective stage of development of said one or more retinopathies, the processor performs multilayer hierarchical classification comprising:
normal versus disease classification;
inter-disease classification; and
stage classification.

9. The AI system of claim 8, wherein the inter-disease classification includes at least diabetic retinopathy (DR) versus sickle cell retinopathy (SCR) classification.

10. The AI system of claim 9, wherein the normal versus disease classification includes at least normal versus DR classification and normal versus SCR classification.

11. The AI system of claim 10, wherein the stage classification includes at least mild, moderate and severe non-proliferative DR (NPDR) stage classification and mild and severe SCR stage classification.

12. The AI system of claim 8, wherein the machine learning algorithm comprises the hierarchical backward elimination algorithm constructed to identify the combinations of retinal features that achieve a best prediction accuracy, to select the identified combinations of retinal features and to configure the classifier model to perform normal versus disease classification, inter-disease classification; and the stage classification based on combinations of retinal features contained in the acquired OCTA data.

13. The AI system of claim 1, wherein the OCTA data comprises an OCTA artery-vein map obtained by:
generating an optical coherence tomography (OCT) artery-vein map from a spectrogram dataset;
generating an OCTA vessel map from the spectrogram dataset;
overlaying the OCT artery-vein map and the OCTA vessel map to generate an overlaid map; and
processing the overlaid map by using the OCT artery-vein map to guide artery-vein differentiation in the OCTA vessel map to generate the OCTA artery-vein map.

* * * * *